(12) United States Patent
Kosugi

(10) Patent No.: US 7,688,950 B2
(45) Date of Patent: Mar. 30, 2010

(54) X-RAY DIAGNOSTIC APPARATUS

(75) Inventor: Norimitsu Kosugi, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/238,044

(22) Filed: Sep. 25, 2008

(65) Prior Publication Data

US 2009/0080618 A1    Mar. 26, 2009

(30) Foreign Application Priority Data

Sep. 25, 2007    (JP) ............... 2007-247206

(51) Int. Cl.
*G21K 5/10*    (2006.01)
*G21K 1/02*    (2006.01)

(52) U.S. Cl. ...................... 378/146; 378/147
(58) Field of Classification Search .......... 378/145–153
See application file for complete search history.

(56) References Cited

U.S. PATENT DOCUMENTS 5,680,434 A * 10/1997 Thelosen et al. ............ 378/150
2005/0069088 A1 * 3/2005 Li ............................. 378/145
2006/0268409 A1 * 11/2006 Tan et al. .................... 359/487

FOREIGN PATENT DOCUMENTS

JP    2008-29645    2/2008

\* cited by examiner

*Primary Examiner*—Irakli Kiknadze
(74) *Attorney, Agent, or Firm*—Oblon, Spivak, McClelland, Maier & Neustadt, L.L.P.

(57) ABSTRACT

When distance compute unit 81 received the instruction of the moving destination at the center of the exposure field 4*a* from center transfer operation unit 74, calculates the moving amount. Operating information processing unit 8 sends beam-limiting control unit 62 the calculated moving amount. Upside beam-limiting control unit 63 to right side beam-limiting control unit of beam-limiting control unit 62 makes the moving amount at the center of the exposure field 4*a* prescribed-times ((H1/H2) times in FIG. 3), calculates the moving amount of each diaphragm blade unit 51 in the upper part, the lower side, and the left part and the right part respectively.

10 Claims, 20 Drawing Sheets

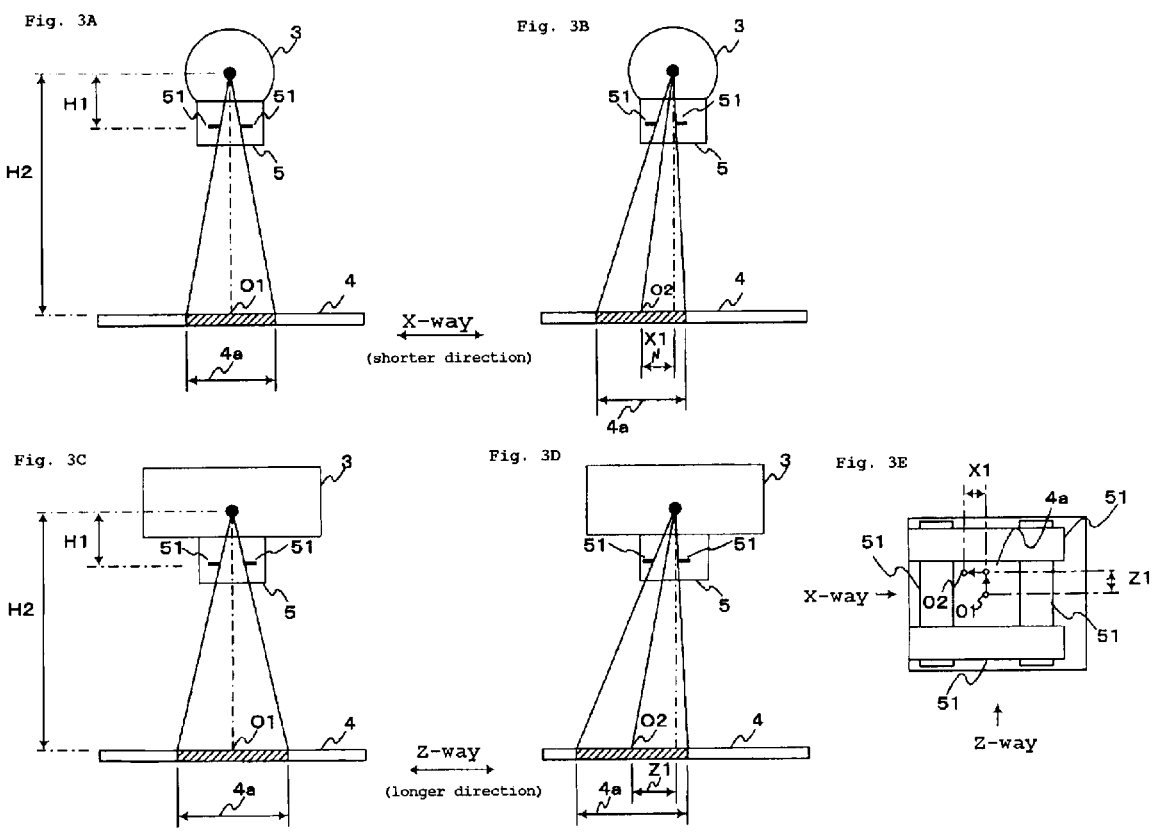

X-RAY DIAGNOSTIC APPARATUS

CROSS-REFERENCE TO RELATED APPLICATIONS

This application is based upon and claims the benefit of priority from prior Japanese Patent Application No. 2007-247206, filed Sep. 25, 2007, the entire contents of which are incorporated herein by reference.

BACKGROUND OF THE INVENTION

1. Field of the Invention

The present invention relates to an X-ray diagnostic apparatus, and particularly relates to setting of a radiation field of X-rays.

2. Description of the Related Art

Traditional X-ray diagnostic apparatus generally comprises a tabletop, an X-ray tube, and an X-ray detector. The tabletop is put a subject, the X-ray tube irradiates X-rays, and the X-ray detector detects X-rays that permeate the subject. The X-ray tube and X-ray detector are arranged on both sides of the tabletop. X-ray detecting elements are arranged to the detection range of the X-ray detector that detects X-rays.

A retention feature maintains the X-ray tube. The X-ray tube is composed movable along longer direction of the tabletop (direction of body axis of a subject) through the retention feature. The X-ray detector moves with the X-ray tube in a unified manner. The tabletop is composed movable along shorter direction of own.

A controller moves the tabletop, the retention feature, and the X-ray detector respectively according to the above-mentioned composition, and the center of the detection range of the X-ray detector can be matched to a test object of subject on the tabletop.

Four diaphragm blade units are located between the X-ray tube and the tabletop. A pair of diaphragm blade unit in the longer direction moves antithetically in the longer direction of the tabletop as a center of the detection range of the X-ray detector. A pair of diaphragm blade unit in the shorter direction moves antithetically in the shorter direction of the tabletop as a center of the detection range of the X-ray detector. Each a pair of diaphragm blade unit narrows the detection range of the X-ray detector from the longer direction of the tabletop and the shorter direction of the tabletop, and forms the exposure field on the X-ray detector. The diaphragm blade unit narrows the detection range of the X-ray detector, cuts unnecessary X-rays, prevents unnecessary radiation exposure, and improves the image quality of the radiographic view.

In the diagnostic radiography, first, an operator matches the center of the detection range of the X-ray detector to the test object of Subject. Concretely, the X-ray tube and the X-ray detector move to the longer direction of the tabletop, and the tabletop moves to the shorter direction of own. Next, the operator confirms the area in the detection range of the X-ray detector to the inspection object of the subject.

When the detection range of the X-ray detector is wide compared with the inspection object of the subject, it is necessary to narrow the detection range of the X-ray detector. Then, the diaphragm blade unit narrows the detection range of the X-ray detector and forms the exposure field on the X-ray detector. Next, the X-ray tube irradiates X-rays to the subject, the X-ray detector detects X-rays that passed the subject, the radiographic view is made and is displays it in the monitor.

When the test object of the subject is changed, the controller moves the tabletop, the retention feature, and the X-ray detector respectively to match the center of the detection range of the X-ray detector to the test object after it changes.

However, when the retention feature is moved, the center of the detection range of the X-ray detector might not be able to be matched to the test object of the subject, because the retention feature have a constant movement stroke's and evades interference with the tabletop etc. the retention feature, and the movement of the retention feature is limited. The retention feature is not stopped easily at a prescribed position, and there is a problem that easily matching the center of the detection range of the X-ray detector to the test object after it changes becomes difficult because the inertia of the retention feature is large. There is a problem of becoming a large encumbrance for the subject when the endoscope is inserted in the inside of the body of subject on the tabletop when the tabletop is moved.

When the test object of the subject is changed within the detection range of the X-ray detector, it only has to operate each a pair of diaphragm blade unit and to expand the exposure field. The test object of the subject can be fit in the broadening exposure field. As a result, the retention feature need not move. However, the retention field expands and outside of test object is unnecessarily exposed to radiation.

To correspond to the change of test object of the subject without expanding exposure field, the controller open and shut each a pair of diaphragm blade unit individually, to move exposure field within the detection range of the X-ray detector, and to match the center of exposure field to the test object of the subject.

However, a past device has the problem that the operation of the diaphragm blade unit becomes complex, because it needs the opening and closing operation of each diaphragm blade unit to do the opening and closing movement individually as for each diaphragm blade unit.

As for a past technology, the X-ray tube and the X-ray detector are composed as one body and rotatably. When it changes the test object of the subject, the X-ray tube and the diaphragm blade unit are rotated as one body, and moves the center of the exposure field to the test object after it changes.

As for a past technology, it has an edge detector of the edge of the X-ray detector and rotates as one body the X-ray tube and diaphragm blade unit, and moves the center of the exposure field. When the edge of the exposure field of X rays hangs to the edge detector, one side of a pair of diaphragm blade unit is individually moved from the edge to the center, and the controller limits it so that an X-ray beam doesn't exceed the detection range of the X-ray detector.

However, the above-mentioned technology needs the mechanism that composes the X-ray tube and diaphragm blade unit as one body and rotatably. It needs the other mechanism to drive the mechanism.

BRIEF SUMMARY OF THE INVENTION

Accordingly, an advantage of an aspect of the present invention is to provide the X-ray diagnostic apparatus that the center of the exposure field can be easily matched to the inspection object of subject and unnecessary exposure of test object of subject can be suppressed.

In order to achieve the above-described advantage, a first aspect of the invention may comprise a tabletop configured to put on a subject; a X-ray tube configured to irradiates X-rays; a X-ray detector configured to detect X-rays that penetrate subject and to arrange on the other side of the X-ray tube; a pair of diaphragm blade unit of a longer direction and a pair of diaphragm blade unit of a shorter direction configured to form a exposure field on X-ray detector and arrange between the tabletop and the X-ray tube; a beam-limiting drive unit configured to drive the each diaphragm blade unit individually; a beam-limiting control unit configured to receive a information of a moving amount and a moving direction when a center of the exposure field moves and to control the beam-limiting drive unit and to move the each diaphragm blade unit individually and to form the exposure field of the moving center is concentric.

In order to achieve the above-described advantage, a sixth aspect of the invention may comprise a tabletop configured to put on a subject; a X-ray tube configured to irradiates X-rays; a X-ray detector configured to detect X-rays that penetrate subject and to arrange on the other side of the X-ray tube; a pair of diaphragm blade unit of a longer direction and a pair of diaphragm blade unit of a shorter direction configured to form a exposure field on X-ray detector and arrange between the tabletop and the X-ray tube; a beam-limiting drive unit configured to drive the each diaphragm blade unit individually; a imaging system drive unit comprised to drive the tabletop, the X-ray tube, and X-ray detector respectively so that the detection range of X-ray detector is relative movement in the longer direction and the shorter direction of the tabletop; an aperture information holding unit comprised to hold aperture information of the longer direction provided beforehand and aperture information of the shorter direction provided beforehand; a center transfer operation unit comprised to indicate the moving direction of the center of exposure field; a judgment unit comprised to judge whether part or all in the exposure field exceed the detection range of X-ray detector or part or all the exposure field enter a operation switching area formed the edge of detection range based on a moving amount and a moving direction information of center of the exposure field and an aperture information held on the aperture information holding unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a figure of a diaphragm blade unit etc. were seen from Z-way;

FIGS. 3B and 3D are figure for explaining the mode that the diaphragm blade unit moves individually;

FIG. 3C is a figure of a diaphragm blade unit etc. were seen from X-way;

FIG. 3E is a plan view of a diaphragm blade unit etc.;

DETAILED DESCRIPTION OF THE INVENTION

Embodiment 1

Figure 1:
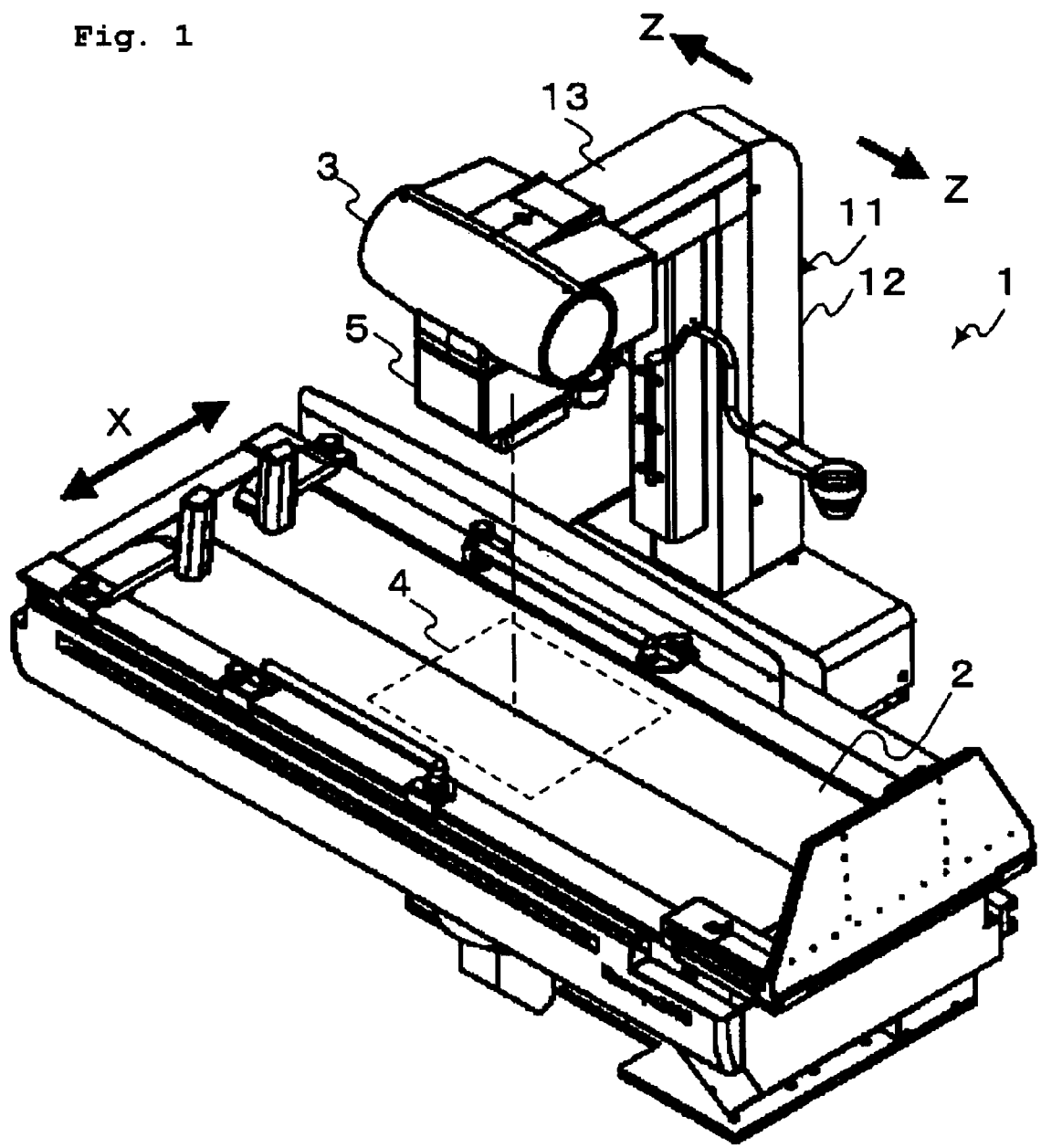
FIG. 1 is an oblique perspective figure of an X-ray diagnostic apparatus according to a first embodiment.

A first embodiment in accordance with the present invention will be explained with reference to FIGS. 1 to 11. FIG. 1 is an oblique perspective figure of an X-ray diagnostic apparatus according to a first embodiment.

As shown in FIG. 1, a X-ray diagnostic apparatus 1 is composed tabletop 2 that puts a subject, a X-ray tube 3 that irradiates X-rays, a X-ray detector 4 that detects X-rays that passed the subject, and a beam-limiting device 5 that forms the exposure field of X-rays to X-ray detector 4. X-ray tube 3 and X-ray detector 4 are put on both sides of tabletop2.

Tabletop 2 is composed movable in a shorter direction of tabletop 2 (X-way in FIG. 1). The shorter direction of tabletop 2 is an orthogonal direction in the direction of body axis of a subject. The longer direction of tabletop2 (Z-way in FIG. 1) is equal to the direction of the direction of body axis of a subject.

X-ray tube 3 is maintained in a retention feature 11. Retention feature 11 has a brace 12 that run on a rail and a lateral-arm 13 that move up and down along brace 12. X-ray tube 3 is fit in an apical end of lateral-arm 13. Beam-limiting device 5 is maintained in lateral-arm 13. X-ray tube 3 and beam-limiting device 5 are composed movable through retention feature 11 along the longer direction of tabletop 2 (Z-way in FIG. 1). X-ray detector 4 is composed movable with X-ray tube 3 and beam-limiting device 5 as one body.

By the above-mentioned composition, X-ray tube 3, X-ray detector 4, and beam-limiting device 5 are composed that a relative movement is possible to tabletop 2 in the longer direction and the shorter direction. When the operator changes the test object of the subject on tabletop 2, and the changed test object comes off from the detection range of X-ray detector 4, the controller moves X-ray tube 3, X-ray detector 4, and beam-limiting device to tabletop 2 respectively and the center of the detection range of X-ray detector 4 is matched to the changed test object.

According to the first embodiment, when the changed test object is in the detection range of X-ray detector 4, the controller operates beam-limiting device 5, and moves the center of the exposure field, and matches the center of the exposure field to the changed test object. In this case, the controller moves X-ray tube 3, X-ray detector 4, and beam-limiting device to tabletop 2 respectively and the center of the detection range of X-ray detector 4 is matched to the changed test object.

Figure 2A:
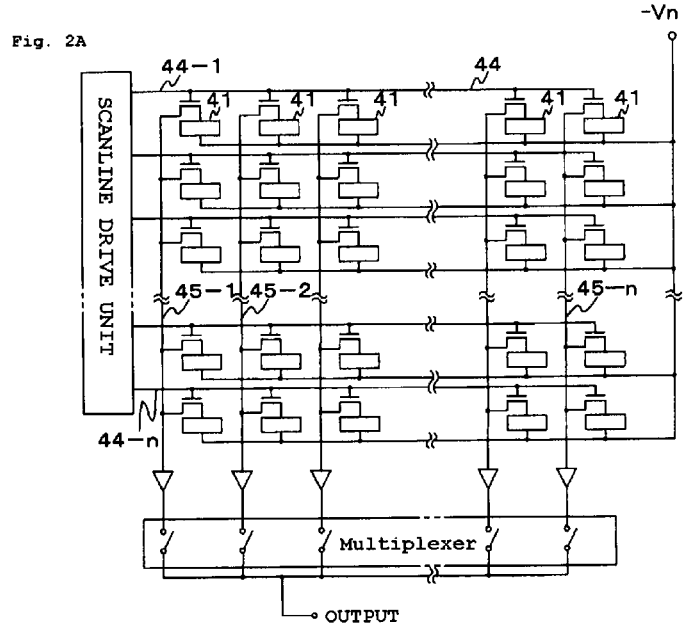
FIG. 2A is a circuit diagram of an X-ray detector.
Figure 2B:
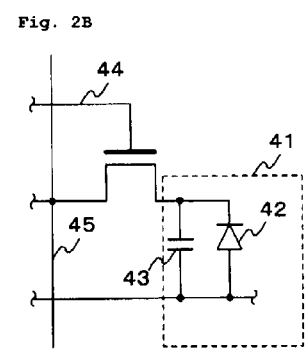
FIG. 2B is a circuit diagram of an X-ray detecting element.

FIG. 2A is a circuit diagram of an X-ray detector, FIG. 2B is a circuit diagram of an X-ray detecting element. X-ray detector 4 is classified into a direct conversion formula and an indirect conversion formula by a X-ray detection formula. The direct conversion formula is a method to use the material that converts the x-ray energy into the charge as a X-ray detecting coat. The indirect conversion formula is a method to convert X-rays into light once, and to convert the light into the charge-signal by the light-receiving element such as photodiodes.

The X-ray detection formula of X-ray detector 4 is the indirect conversion formula. As shown in FIG. 2A, multi line and row X-ray detecting elements are distributed to the detection range of X-ray detector 4 that detects X-rays. The X-ray has the element 41 that detecting elements convert X-rays into optical-wavelength, and forms the charge corresponding to quantities of light of optical-wavelength.

As shown in FIG. 2B, each elements 41 is composed a photodiode 42 that picks up the optical-wavelength and forms the charge corresponding to incident light volume, and a capacitor 43 accumulates the charge formed from photodiode 42. The charge accumulated in the capacitor 43 is read out as imaging signal in each element sequentially from topmost scan line 44-1 to topmost signal line 45-1 through a scan line 44. An image signal is converted into a X-ray image-data where image-data lined up in an element alignment coordinate system in read order. X-ray image-data is maintained in a fluorography image memory 94, and displayed in a monitor 95. Fluorography image memory 94 and monitor 95 are described later.

Beam-limiting device 5 is explained in reference to FIGS. 1 and 3. FIGS. 3A to 3E are a figure for explaining X-ray tube 3, X-ray detector 4, and beam-limiting device 5. As shown in FIGS. 3A to 3E, beam-limiting device 5 is equipped between tabletop 2 and X-ray tube 3. Beam-limiting device 5 has an above and below pair of diaphragm blade unit 51 and a right and left pair of diaphragm blade unit 51.

FIG. 3A is a figure of a diaphragm blade unit 51 etc. were seen from Z-way (the longer direction of tabletop 2). As shown in FIG. 3A, a right and left pair of diaphragm blade unit 51 narrows the detection range of X-ray detector 4 from the shorter direction of tabletop 2 (X-way), and forms the exposure field on X-ray detector 4. When the center of the exposure field is moved in the X-way, right and left pair of diaphragm blade unit 51 moves the prescribed-times of the moving amount to X-way. FIG. 3B is figure for explaining the mode that moved center of exposure field in the X-way. A right and left pair of diaphragm blade unit 51 corresponds to a pair of diaphragm blade unit 51 in the shorter direction.

FIG. 3C is a figure of a diaphragm blade unit etc. were seen from X-way. As shown in FIG. 3C, an above and below pair of diaphragm blade unit 51 narrows the detection range of X-ray detector 4 from the longer direction of tabletop 2 (Z-way), and forms the exposure field on X-ray detector 4. When the center of the exposure field is moved in the Z-way, above and below pair of diaphragm blade unit 51 moves the prescribed-times of the moving amount to Z-way. FIG. 3D is figure for explaining the mode that moved center of exposure field in the Z-way. An above and below pair of diaphragm blade unit 51 corresponds to a pair of diaphragm blade unit 51 in the longer direction.

For example, a distance from a focus of X-ray tube 3 to diaphragm blade unit 51 is assumed to be H1, and a distance from a focus of X-ray tube 3 to X-ray detector 4 is assumed to be H2. The amount of the movement to the X-way or the Z-way of each diaphragm blade unit 51 is (H1/H2) times the amount of the movement at the center of the exposure field.

Figure 4:
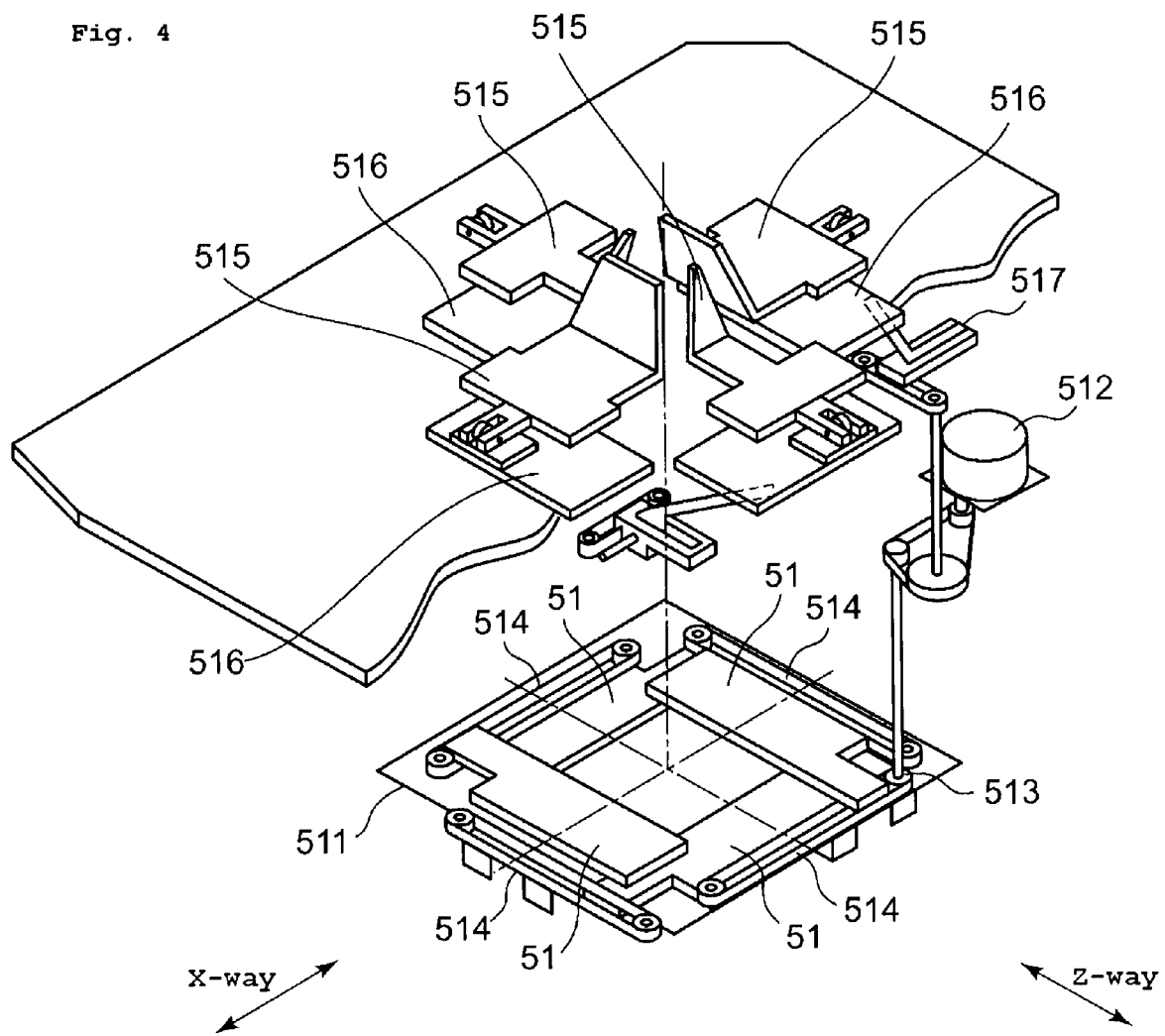
FIG. 4 is a exploded perspective view of a beam-limiting device.
Figure 5:
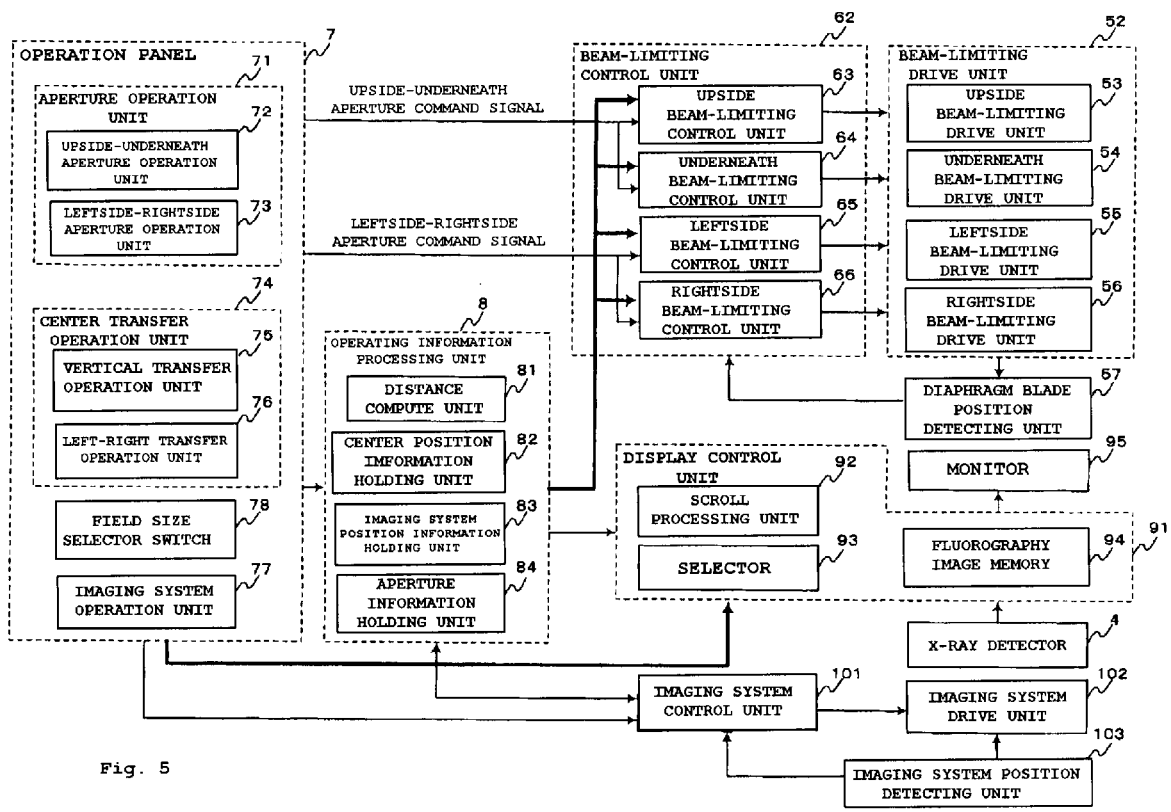
FIG. 5 is a functional block diagram of the X-ray diagnostic apparatus.

Detail of Beam-limiting device 5 is explained in reference to FIG. 4. FIG. 4 is an exploded perspective view of a beam-limiting device. As shown in FIG. 5, beam-limiting device 5 are arranged a pair of diaphragm blade unit 51 in the Z-way (the longer direction) and a pair of diaphragm blade unit 51 in the X-way (the shorter direction) on a base component 511.

The combination of a stepping motor 512, a back-diaphragm blade 515, a lower-diaphragm blade 516, and a block 517 is arranged above each diaphragm blade unit 51 respectively. The amount of the rotation of the stepping motor 512 transmits to diaphragm blade unit 51 through a pulley 513 and the driving belt 514. The amount of the rotation of the stepping motor 512 transmits to back-diaphragm blade 515 and lower-diaphragm blade 516 through block 517.

According to the above-mentioned composition, diaphragm blade unit 51, back-diaphragm blade 515, and lower-diaphragm blade 516 corresponding to stepping motor 512 move to the X-way or the Z-way by a prescribed amount according to the amount of the rotation of stepping motor 512.

A rectangular exposure field is formed on X-ray detector 4 by each diaphragm blade unit 51. The medial edge in each diaphragm blade unit 51 corresponds to each edge of the exposure field. Each diaphragm blade unit 51, each back-diaphragm blade 515, each lower-diaphragm blade 516, and X-ray shield unit cover X-rays so that X-rays irradiated from X-ray tube 3 are not irradiated except the exposure field.

Composition in which each diaphragm blade unit 51 is individually driven will be explained in reference to FIG. 5. FIG. 5 is a functional block diagram of the X-ray diagnostic apparatus. As shown in FIG. 5, X-ray diagnostic apparatus 1 has a beam-limiting drive unit 52 that individually drives each diaphragm blade unit 51 and a beam-limiting control unit 62 that controls beam-limiting drive unit 52.

Beam-limiting drive unit 52 has an upside beam-limiting drive unit 53, an underneath beam-limiting drive unit 54, a left side beam-limiting drive unit 55, and a right side beam-limiting drive unit 56 to drive each diaphragm blade unit 51 severally. Upside beam-limiting drive unit 53 and underneath beam-limiting drive unit 54 individually drive each diaphragm blade unit 51 of upper and lower, and narrow the detection range of X-ray detector 4 from the longer direction of tabletop 2 (the Z-way). Left side beam-limiting drive unit 55 and right side beam-limiting drive unit 56 individually drive each diaphragm blade unit 51 of left side and right side, and narrow the detection range of X-ray detector 4 from the shorter direction of tabletop 2 (the X-way).

Beam-limiting control unit 62 has an upside beam-limiting control unit 63, an underneath beam-limiting control unit 64, a left side beam-limiting control unit 65, and right side beam-limiting control unit 66 to control upside beam-limiting drive unit 53, underneath beam-limiting drive unit 54, left side beam-limiting drive unit 55, and right side beam-limiting drive unit 56 severally.

A basic composition of upside beam-limiting drive unit 53 to right side beam-limiting drive unit 56 is the same. A basic composition of upside beam-limiting control unit 63 to right side beam-limiting control unit 66 is the same.

Upside beam-limiting drive unit 53 and upside beam-limiting control unit 63 will explained on behalf of beam-limiting drive unit 52 and beam-limiting control unit 62. The explanation of underneath beam-limiting drive unit 54, left side beam-limiting drive unit 55, right side beam-limiting drive unit 56, underneath beam-limiting control unit 64, a left side beam-limiting control unit 65, and right side beam-limiting control unit 66 is omitted.

Upside beam-limiting drive unit 53 has stepping motor 512 in FIG. 4. X-ray diagnostic apparatus has a diaphragm blade position detecting unit 57 that is the encoder that detects the amount of the rotation corresponding to the stepping motor.

Upside beam-limiting control unit 63 calculates a pulse-member data that corresponds to the amount of the rotation of the stepping motor of upside beam-limiting drive unit 53 based on the moving amount of diaphragm blade unit 51. Upside beam-limiting control unit 63 generates a command pulse signal based on a pulse-member data, converts a generated command pulse signal into a power current, and thrown to the stepping motor.

The moving amount of diaphragm blade unit 51 receives the instruction of the moving destination at the center of the exposure field and is calculated. An operator operates a center transfer operation unit 74, and the moving destination at the center of the exposure field is directed.

Next, an operation panel 7 will be explained. Operation panel 7 is installed in a control booth. As shown in FIG. 5, operation panel 7 has aperture operation unit 71, center transfer operation unit 74, an imaging system operation unit 77, and a field size selector switch 78.

Figure 6A:
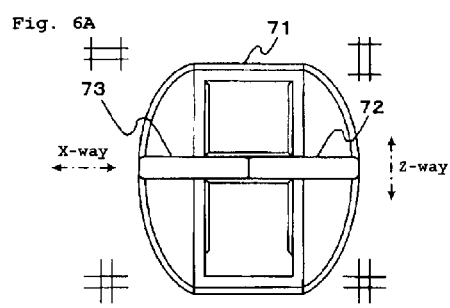
FIG. 6A is a elevation view of a aperture operation unit.

Aperture operation unit 71 will be explained in reference to FIGS. 6A to 6D. FIG. 6A is an elevation view of an aperture operation unit. Aperture operation unit 71 has an upside-underneath aperture operation unit 72 that is switching operation a pair of diaphragm blade unit 51 in the longer direction of tabletop 2 (Z-way) and left side-right side aperture operation unit 73 that is switching operation a pair of diaphragm blade unit 51 in the shorter direction of tabletop 2 (X-way).

Figure 6B:
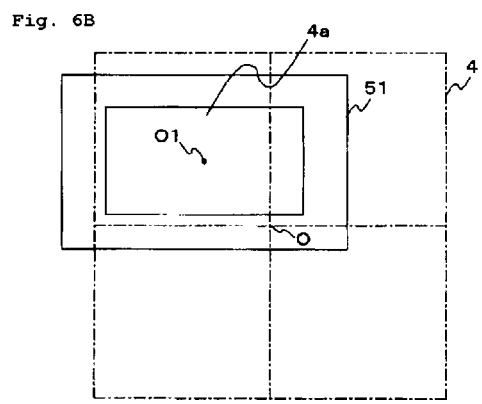
FIGS. 6B to 6D are figure of relation between the diaphragm blade unit that opening and closing operation is done by the aperture operation unit and exposure field.
Figure 6C:
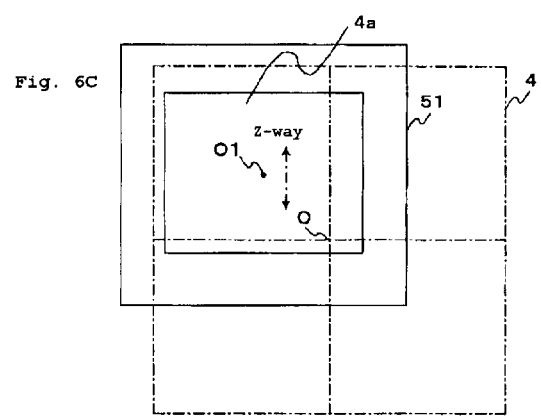
Figure 6D:
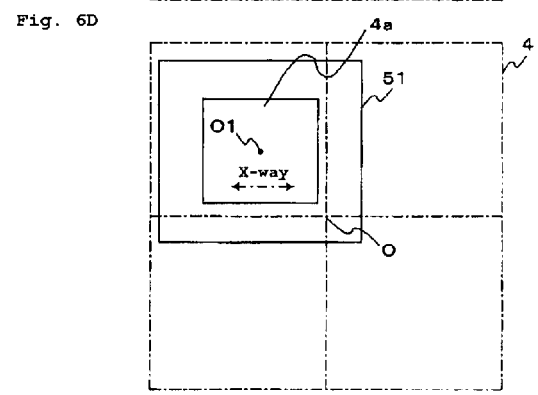

FIGS. 6B to 6D are figures of relation between the diaphragm blade unit that opening and closing operation is done by the aperture operation unit and exposure field. FIG. 6B is figure for explaining the mode that diaphragm blade unit 51 forms the exposure field 4a on X-ray detector 4. The center of the detection range of X-ray detector 4 is at position O. The center of the exposure field 4a is at position O1. In FIG. 6B, each diaphragm blade unit 51 is shown as a unit. Each diaphragm blade unit 51 is shown expanded at prescribed-times (H2/H1 in FIG. 3) on X-ray detector 4. In FIGS. 6C and 6D as well as FIG. 6B, each diaphragm blade unit 51 is shown expanded at prescribed-times.

When the exposure field 4a is a state shown in FIG. 6b, upside-underneath aperture operation unit 72 outputs an upside-underneath aperture command signal to upside beam-limiting control unit 63 and an underneath beam-limiting control unit 64. Upside beam-limiting control unit 63 and an underneath beam-limiting control unit 64 operates upside beam-limiting drive unit 53 and underneath beam-limiting drive unit 54 respectively based on the upside-underneath aperture command signal. As shown in FIG. 6C, the distance (the aperture) between above and below diaphragm blade unit 51 that is opened on the longer direction of tabletop 2 (Z-way) changes. In this case, the position of the center O1 of the exposure field 4a doesn't move.

When the exposure field 4a is a state shown in FIG. 6b, left side-right side aperture operation unit 73 outputs an left side-right side aperture command signal to left side beam-limiting control unit 65 and right side beam-limiting control unit 66. Left side beam-limiting control unit 65 and right side beam-limiting control unit 66 operates left side beam-limiting drive unit 55 and right side beam-limiting drive unit 56 respectively based on the left side-right side aperture command signal. As shown in FIG. 6D, the distance (the aperture) between left side and right side diaphragm blade unit 51 that is opened on the shorter direction of tabletop 2 (X-way) changes. In this case, the position of the center O1 of the exposure field 4a doesn't move.

Information of the distance (the aperture) between above and below diaphragm blade unit 51 that is opened on the longer direction of tabletop 2 (Z-way) and information of the distance (the aperture) between left side and right side diaphragm blade unit 51 that is opened on the shorter direction of tabletop 2 (X-way) are preserved in an aperture information holding unit 84.

Figure 7A:
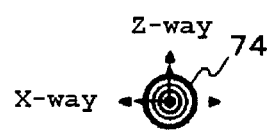
FIG. 7A is a elevation view of a center transfer operation unit.

Center transfer operation unit 74 will be explained in reference to FIGS. 5, 7A and 7B. FIG. 7A is a elevation view of a center transfer operation unit. Center transfer operation unit 74 is put in operation panel 7 in the control booth.

Center transfer operation unit 74 has a vertical transfer operation unit 75 and a left-right transfer operation unit 76. As shown in FIGS. 7A and 7B, the operator operates vertical transfer operation unit 75 and directs the moving destination at the center of the exposure field 4a. A manipulate signal from vertical transfer operation unit 75 is output to an operating information processing unit 8. The manipulate signal corresponds to the moving amount to the longer direction of tabletop 2 (Z-way).

Figure 7B:
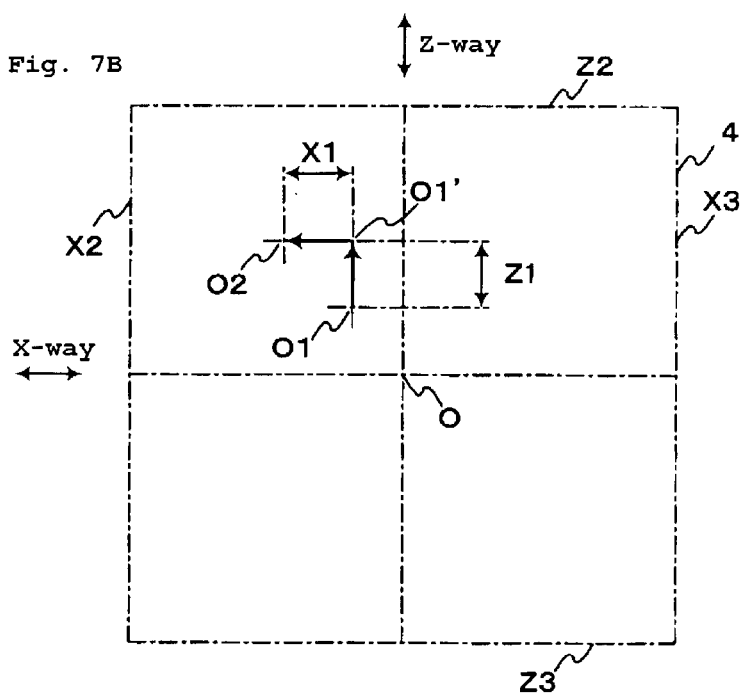
FIG. 7B is a figure for explaining the mode that a center of the exposure field moves.

As shown in FIGS. 7A and 7B, the operator operates left-right transfer operation unit 76 and directs the moving destination at the center of the exposure field 4a. A manipulate signal from left-right transfer operation unit 76 is output to an operating information processing unit 8. The manipulate signal corresponds to the moving amount to the shorter direction of tabletop 2 (X-way).

The operator may operate center transfer operation unit 74 on the obliquely upward and downward. In that case, the manipulate signal from center transfer operation unit 74 is output to operating information processing unit 8 separately for the moving amount to Z-way component (component of the direction of above and below) and the moving amount to X-way component (component of the direction of left and right) element.

FIG. 7B is a figure for explaining the mode that a center of the exposure field moves. As shown in FIG. 7B, the center of the exposure field 4a is the position O1. Operating information processing unit 8 receives the manipulate signal from vertical transfer operation unit 75, calculates the distance Z1 of the Z-way at the center of the exposure field, and output to upside beam-limiting control unit 63 and an underneath beam-limiting control unit 64. Upside beam-limiting control unit 63 and an underneath beam-limiting control unit 64 calculate each distance and direction of motion of above and below diaphragm blade unit 51, and control upside beam-limiting drive unit 53 and underneath beam-limiting drive unit 54. Upside beam-limiting drive unit 53 and underneath beam-limiting drive unit 54 move the above and below diaphragm blade unit 51 respectively by just Z1. And, the center of the exposure field moves from position O1 to position O1'.

Operating information processing unit 8 receives the manipulate signal from left-right transfer operation unit 76, calculates the distance X1 of the X-way at the center of the exposure field, and output to left side beam-limiting control unit 65 and right side beam-limiting control unit 66. Left side beam-limiting control unit 65 and right side beam-limiting control unit 66 calculate each distance and direction of motion of left and right diaphragm blade unit 51, and control left side beam-limiting drive unit 55 and right side beam-limiting drive unit 56. Left side beam-limiting drive unit 55 and right side beam-limiting drive unit 56 move the left and right diaphragm blade unit 51 respectively by just X1. And, the center of the exposure field moves from position O1' to position O2.

Next, an imaging system control unit 101, an imaging system drive unit 102, and an imaging system position detecting unit 103 will be explained.

Imaging system control unit 101 generates the control signal based on the manipulate signal from imaging system operation unit 77, and output to imaging system drive unit 102. Imaging system drive unit 102 has the stepping motor that drives tabletop 2 and has the stepping motor that drives retention feature 11. When each stepping motor of imaging system drive unit 102 begins rotating in a prescribed direction, an imaging system construction moves relativity.

Imaging system position detecting unit 103 detects the amount of the rotation of each stepping motor of imaging system drive unit 102, and it is output to imaging system control unit 101. Imaging system control unit 101 obtains the position of tabletop 2 and the position of X-ray detector 4 respectively from the amount of the rotation of each stepping motor. Information at the position of tabletop 2 and the position of X-ray detector 4 is preserved in an imaging system position information holding unit 83.

Next, operating information processing unit 8 will be explained. Operating information processing unit 8 has a moving amount compute unit 81 that obtains the moving amount and moving direction of center of exposure field 4a, a center position information holding unit 82 that maintains the position information of center of exposure field 4a, imaging system position information holding unit 83, and an aperture information holding unit.

When center transfer operation unit 74 prescribes the moving destination at the center of the exposure field 4a, moving amount compute unit 81 calculates the moving amount and moving direction of center of exposure field 4a from location information before moving of center of exposure field and location information in moving destination at center of exposure field. The location information in the moving destination at the center of the exposure field 4a is preserved in center position information holding unit 82.

Imaging system position information holding unit 83 maintains the location information of tabletop 2 and the location information of X-ray detector 4 that operating information processing unit 8 acquired from imaging system control unit 101.

Operating information processing unit 8 obtains the position O of the center of the detection range of X-ray detector 4 from the location information of tabletop 2 and the location information of X-ray detector 4. Operating information processing unit 8 obtains the edge in the detection range of X-ray detector 4 from the size of the detection range of X-ray detector 4. The edge in the detection range of X-ray detector 4 is the edge in the detection range in the X-way and Z-way. The vicinity of edge of X-way of X-ray detector 4 shows X2 and X3 in FIG. 7B. The vicinity of edge of Z-way of X-ray detector 4 shows Z2 and Z3 in FIG. 7B.

Operating information processing unit 8 obtains the edge of exposure field 4a from location information in moving destination at center of exposure field 4a, information of the distance (the aperture) between left side and right side diaphragm blade unit 51 that is opened on the shorter direction of tabletop 2 (X-way), and information of the distance (the aperture) between above and below diaphragm blade unit 51 that is opened on the longer direction of tabletop 2 (Z-way).

When operating information processing unit 8 receives the instruction of the moving destination at the center of the exposure field from center transfer operation unit 74, operating information processing unit 8 make judgments whether part or all in the exposure field 4a exceed the detection range of X-ray detector 4.

When part or all in the exposure field 4a exceed the detection range of X-ray detector 4, operating information processing unit 8 corrects the moving amount calculated by moving amount compute unit 81 and operating information processing unit 8 outputs the moving amount after correction to beam-limiting control unit 62. Beam-limiting control unit 62 controls beam-limiting drive unit 52 based on the moving amount after correction, and is moves diaphragm blade unit 51. The edge in the exposure field 4a coincides with the edge in the detection range of X-ray detector 4 and the exposure field 4a is set in the detection range of X-ray detector 4. As a result, an unnecessary irradiation outside the detection range of X-ray detector 4 is limited.

Next, composition of a display control unit 91 will be explained in reference to FIG. 5. As shown in FIG. 5, X-ray image-data that be converted the image signal read from X-ray detector is associated with coordinates in the detection range of X-ray detector 4, and preserved in fluorography image memory 94. Display control unit 91 associates the center of the detection range of X-ray detector with a center position in the monitor 95, and displays the detection range of X-ray detector 4. Monitor 95 is set up in the control booth.

Display control unit 91 obtains relative position of exposure field 4a to range of detection of X-ray detector 4 based on the information on the moving amount between each diaphragm blade unit 51 maintained in aperture information holding unit 84 and the location information of the center of the exposure field 4a maintained in center position information holding unit 82, and displays the exposure field 4a at a prescribed position in monitor 95. The operator operates center transfer operation unit 74 while seeing the detection range of X-ray detector 4 and the exposure field 4a displayed in monitor 95.

Display control unit 91 has a scroll processing unit 92. Scroll processing unit 92 associates a center position of the exposure field 4a on X-ray detector 4 with a standard position (For example, it is a center in display) in the display of providing beforehand, and displays the exposure field 4a. As a result, even if the center of the exposure field 4a moves by operating center transfer operation unit 74, the screen of the monitor can follow to the exposure field 4a. An appropriate exposure field 4a can be easily and for a short time selected.

Display control unit 91 has a selector 93. Selector 93 selects the mode that associates center of range of detection of X-ray detector 4 with center position in monitor 95, and displays range of detection of X-ray detector 4 or the mode that associates center of exposure field 4a on X-ray detector 4 with center position in monitor 95, and displays exposure field 4a.

Display control unit 91 receives the instruction signal from the field size selector switch 78, enlarges or reduces a prescribed range in coordinates of the X-ray image-data to the multistep within the range decided beforehand in the display, and displays the X-ray image-data in the monitor 95.

Figure 8:
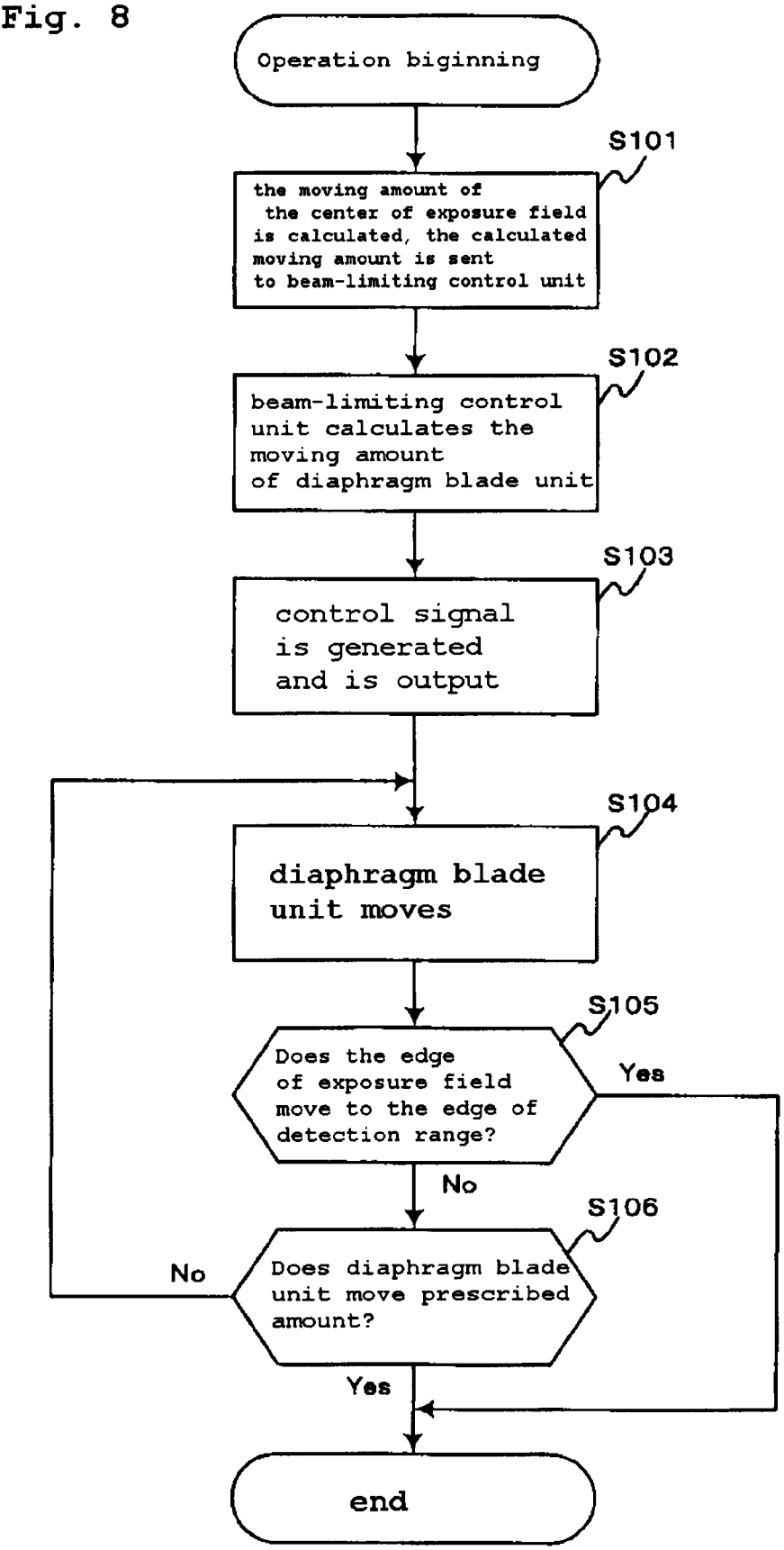
FIG. 8 is a flowchart of procedure of the diaphragm blade unit moves.

Next, procedure for moving diaphragm blade unit 51 will be explained in reference to FIG. 8. FIG. 8 is a flowchart of procedure of the diaphragm blade unit moves.

Figure 9A:
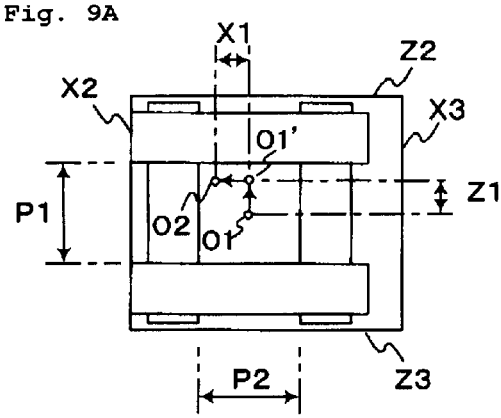
FIGS. 9A to 9C are a figure for explaining the mode that the diaphragm blade unit moves.

As shown in FIG. 8, the operator operates center transfer operation unit 74 while seeing the detection range and the exposure field 4a of X-ray detector 4 displayed in the monitor. For example, as shown in FIG. 9A, the operator prescribes position O1' in the moving destination at the center of the exposure field 4a by center transfer operation unit 7.

When moving amount compute unit 81 received the instruction of the moving destination at the center of the exposure field 4a from center transfer operation unit 74, moving amount compute unit 81 calculates the moving amount (Z1) at the center of the exposure field 4a based on information at the position O1 of the movement origin at the center of the exposure field 4a and the position O1' of the moving destination at the center of the exposure field 4a. The direction of the movement is included in the moving amount (Z1). For example, a positive moving amount is an upper direction, and a negative moving amount is a lower direction. Operating information processing unit 8 sends beam-limiting control unit 62 the calculated moving amount (S101).

Upside beam-limiting control unit 63 to right side beam-limiting control unit 66 of beam-limiting control unit 62 makes the moving amount at the center of the exposure field 4a prescribed-times ((H1/H2) times in FIG. 3), calculates the moving amount of each diaphragm blade unit 51 in the upper part, the lower side, and the left part and the right part respectively (S102).

For example, Upside beam-limiting control unit 63 obtains the amount of the rotation of the stepping motor of upside beam-limiting drive unit 53 from the moving amount of diaphragm blade unit 51. Upside beam-limiting control unit 63 calculates the pulse-member data that corresponds to the amount of the rotation, generates the command pulse signal based on a pulse-member data, converts a generated command pulse signal based on the pulse-member data, converts the command pulse signal into the current, and thrown to the stepping motor (S103).

Upside beam-limiting drive unit 53 moves diaphragm blade unit 51 (S104). Upside beam-limiting control unit 63 judges whether the edge from the position of diaphragm blade unit 51 detected by diaphragm blade position detecting unit 57 to the exposure field 4a moved to the edge Z2 in the detection range of X-ray detector 4 while diaphragm blade unit 51 is moving (S105).

Upside beam-limiting drive unit 53 moves diaphragm blade unit 51 continuous when upside beam-limiting control unit 63 judges that the edge in the exposure field 4a doesn't move to the edge Z2 in the detection range of X-ray detector 4 (S105; NO). When upside beam-limiting drive unit 53 move diaphragm blade unit 51 prescribed amount (S106; Yes), Upside beam-limiting drive unit 53 stops moving of diaphragm blade unit 51.

As explained above, when the operator operates center transfer operation unit 74 and the moving destination at the center of the exposure field 4a is directed, each diaphragm blade unit 51 follows to the movement of the center of the exposure field 4a. And, the center of the exposure field 4a can be easily matched to the test object of subject after is changed. An appropriate exposure field 4a can be easily selected for a short time without moving tabletop 2, retention feature 11, and X-ray detector 4.

When upside beam-limiting control unit 63 judges that the edge of exposure field 4a moves to the edge Z2 of detection range of X-ray detector 4 (S105; Yes), upside beam-limiting drive unit 53 stops moving of diaphragm blade unit 51. A part of the exposure field 4a isn't go over the detection range of X-ray detector 4, and the unnecessary exposure place run out.

Similarly, underneath beam-limiting control unit 64, left side beam-limiting control unit 65, and right side beam-limiting control unit 66 control underneath beam-limiting drive unit 54, left side beam-limiting drive unit 55, and right side beam-limiting drive unit 56 severally. After underneath beam-limiting drive unit 54, left side beam-limiting drive unit 55, and right side beam-limiting drive unit 56 moves prescribed amount each diaphragm blade unit 51, it is stopped. Part or all of exposure field 4a does not exceed detection range of X-ray detector 4 and each diaphragm blade unit 51 becomes states in FIG. 9B.

Operating information processing unit 8 calculates the movement amount and the movement direction of the center of exposure field 4a until the edge of the exposure field 4a matches the edge of the detection range of X-ray detector 4. The calculated moving amount etc. is sent to beam-limiting control unit 62, beam-limiting control unit 62 may controls beam-limiting drive unit 52. Part of exposure field 4a does not exceed detection range of X-ray detector 4 and a useless irradiation place can be lost.

Figure 9B:
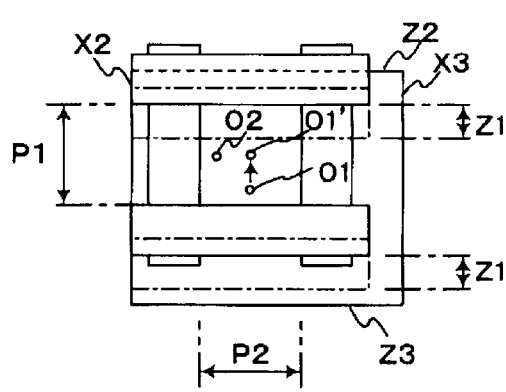
Figure 9C:
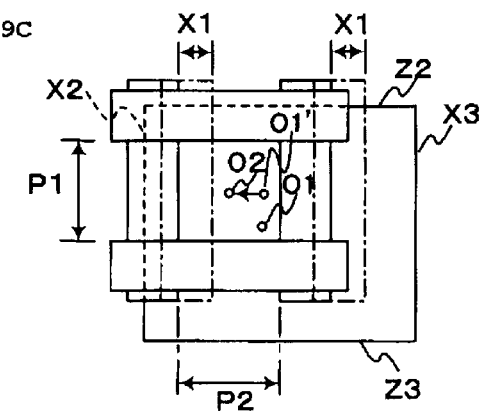

As shown in FIG. 9B, when center transfer operation unit 74 prescribes position of moving destination at center of exposure field 4a, upside beam-limiting control unit 63, underneath beam-limiting control unit 64, left side beam-limiting control unit 65, and right side beam-limiting control unit 66 control upside beam-limiting drive unit 53, underneath beam-limiting drive unit 54, left side beam-limiting drive unit 55, and right side beam-limiting drive unit 56 severally. After upside beam-limiting drive unit 53, underneath beam-limiting drive unit 54, left side beam-limiting drive unit 55, and right side beam-limiting drive unit 56 moves prescribed amount each diaphragm blade unit 51, it is stopped. Each diaphragm blade unit 51 becomes states in FIG. 9C.

When left side beam-limiting control unit 65 judges that the edge of exposure field 4a moves the edge X2 of detection range of X-ray detector 4, left side beam-limiting drive unit 55 stops moving of diaphragm blade unit 51. A useless irradiation place can be lost.

When underneath beam-limiting control unit 64 judges that the edge of exposure field 4a moves the edge Z3 of detection range of X-ray detector 4, underneath beam-limiting drive unit 54 stops moving of diaphragm blade unit 51. When right side beam-limiting control unit 66 judges that the edge of exposure field 4a moves the edge X3 of detection range of X-ray detector 4, right side beam-limiting drive unit 56 stops moving of diaphragm blade unit 51. A useless irradiation place can be lost.

When the test object of subject after is changed enters detection range of X-ray detector 4, to be suitable for the test object of the center of the exposure field 4a, the center of the exposure field 4a in the moving destination may be directed by center transfer operation unit 47.

When the test object of subject after is changed exceeds detection range of X-ray detector 4, tabletop 2, retention feature 11, and X-ray detector 4 do relative movement. Specifically, tabletop 2 moves the shorter direction (X-way), X-ray tube 3, X-ray detector 4, and beam-limiting device 5 move the longer direction of tabletop 2 (Z-way).

Figure 10:
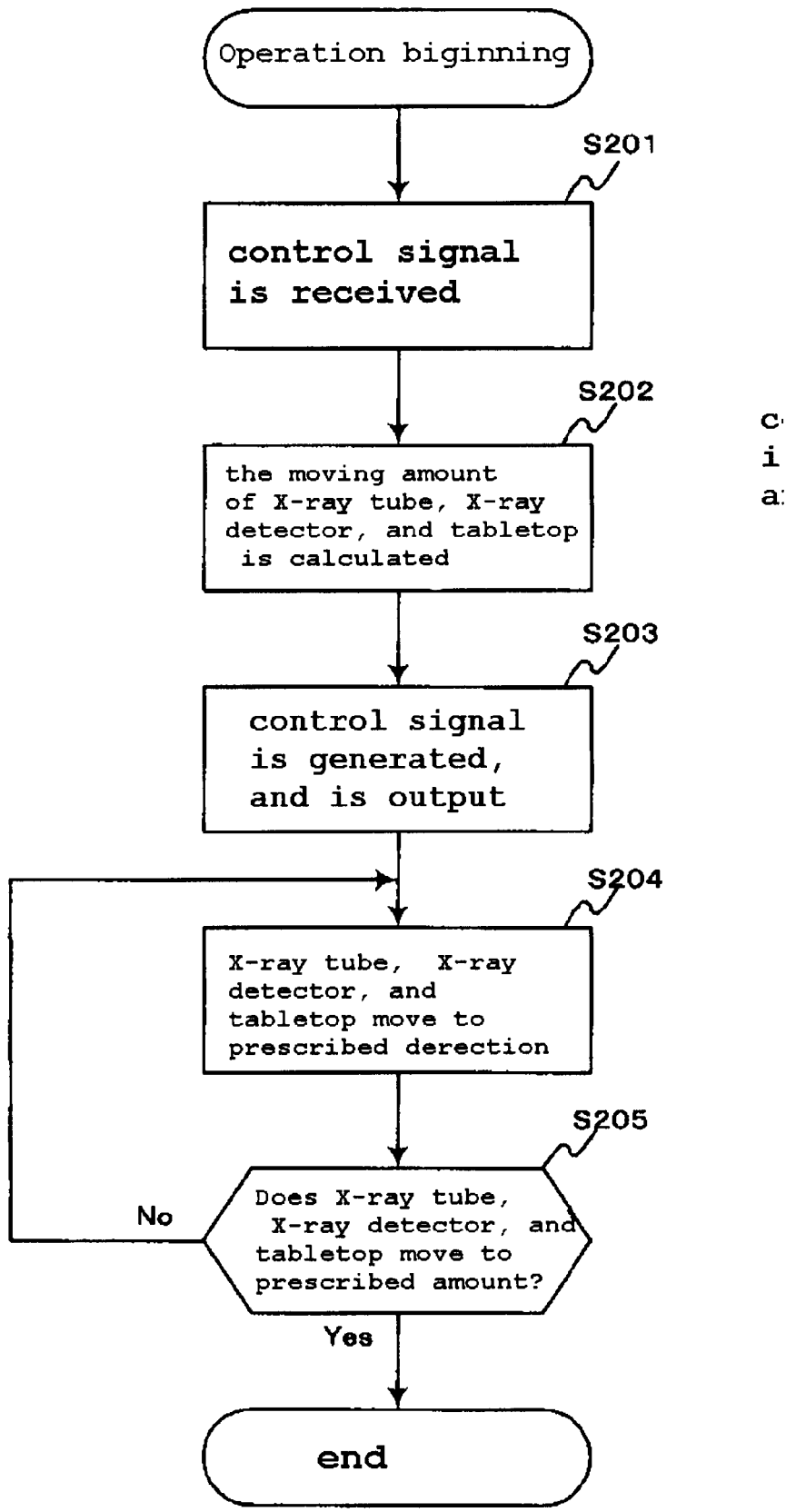
FIG. 10 is a flowchart of procedure of a imaging system construction is relative movement.

Procedure for matching center of detection range of X-ray detector 4 to test object of subject after is changed will be explained in reference to FIG. 10. FIG. 10 is a flowchart of procedure of imaging system construction is relative movement.

Figure 11A:
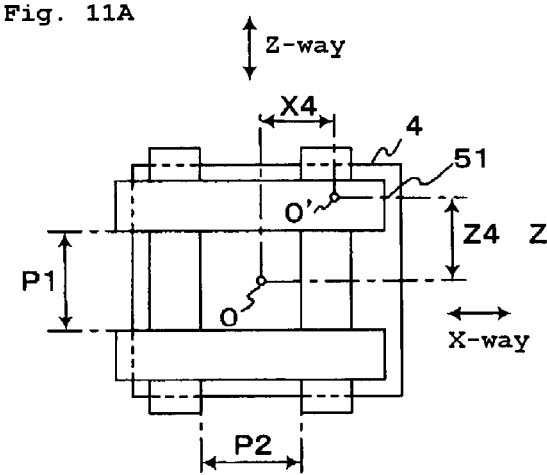
FIGS. 11A and 11B are figure for explaining the mode that a imaging system construction is relative movement.

As shown in FIG. 11A, when the center of detection range of X-ray detector 4 is position O, imaging system operation unit 77 directs position O' of moving destination at center.

As shown in FIG. 10A, imaging system control unit 101 receives position O' of moving destination at center of detection range of X-ray detector 4 (S201). Imaging system control unit 101 calculates the amount of relative movement of imaging system structure from the moving amount and the moving direction of the center of detection range of X-ray detector 4. Specifically, imaging system control unit 101 calculates the moving amount where X-ray tube 3 and X-ray detector 4 move along direction of Z-way and the moving amount where tabletop 2 moves X-way (S202).

Imaging system control unit 101 generates the control signal from the calculated moving amount of X-ray tube 3 etc. and the moving amount of tabletop 2, and output to imaging system drive unit 102 (S203). X-ray tube 3, X-ray detector 4, and beam-limiting device 5 move along the longer direction of tabletop 2 (Z-way) as one body. Tabletop 2 moves the shorter direction (X-way) (S204).

When X-ray tube 3, X-ray detector 4, and beam-limiting device 5 move the prescribed amount (S205; Yes), imaging system drive unit 102 stops moving of X-ray tube 3 etc., and stops moving tabletop 2.

Figure 11B:
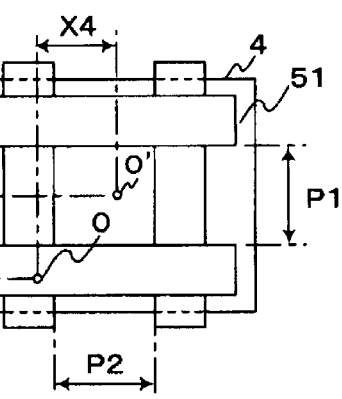

And, the center of the exposure field 4a can be easily matched to the test object of subject after is changed. FIG. 11B shows the states that the center of detection range of X-ray detector 4 becomes the position O' by relative movement of imaging system structure.

Embodiment 2

Figure 12:
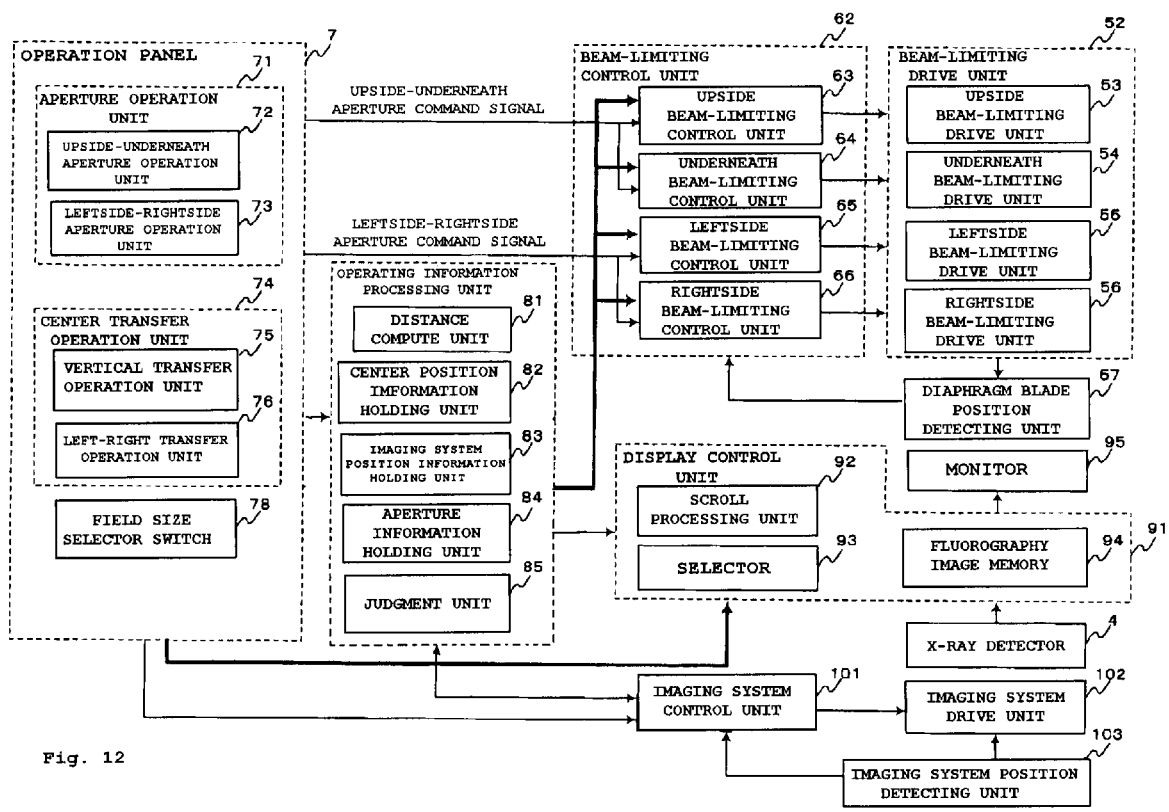
FIG. 12 is a functional block diagram of the X-ray diagnostic apparatus according to a second embodiment.

A second embodiment in accordance with the present invention will be explained with reference to FIG. 12. FIG. 12 is a functional block diagram of the X-ray diagnostic apparatus according to a second embodiment. The second embodiment is different from the first embodiment in the following two points.

The first different point is the relative movement of imaging system structure by operating of center transfer operation unit 74.

In the second embodiment, the moving destination at the center of the exposure field is directed by operating center transfer operation unit 74. To locate the center of the exposure field in the moving destination at the directed center, imaging system structure is relative movement.

The second different point is operating information processing unit 8 has judgment unit 85. Judgment unit 85 judges whether part or all in the exposure field 4a exceed the detection range of X-ray detector 4 when the center of exposure field 4a move based on the position of edge of exposure field 4a and the position of edge of detection range of X-ray detector. Operating information processing unit 8 decides the relative movement of imaging system structure or moving of beam-limiting unit 5 based on the result of judgment unit 85.

Operating information processing unit 8 has moving amount compute unit 81, center position information holding unit 82, imaging system position information holding unit 83, and aperture information holding unit 84. Moving amount compute unit 81 receives direction from center transfer operation unit 74, calculates the moving amount and the moving direction of the center of exposure field 4a. Center position information holding unit 82 holds the position information of the center of exposure field 4a. Imaging system position information holding unit 83 holds the each position information of tabletop 2 and X-ray detector 4. Aperture information holding unit 84 holds the distance (aperture) between each diaphragm blade unit 51.

Operating information processing unit 8 calculates position of moving destination at center of exposure field 4a and position of edge of exposure field 4a from the moving amount and moving direction of the center of exposure field 4a, location information of movement origin at center of exposure field 4a, and information on the distance (aperture) between each diaphragm blade unit 51.

Operating information processing unit 8 calculates the center position and the position of edge of detection range of X-ray detector 4 side (position of about four in rectangular detection range) from the information of each position of tabletop 2 and X-ray detector 4.

When Judgment unit 85 judges that exposure field 4a enters the detection range of X-ray detector 4 by moving of the center of exposure field 4a, operating information processing unit 8 send the moving amount and the moving direction of the exposure field 4a to beam-limiting control unit 62. Beam-limiting control unit 62 controls beam-limiting drive unit 52, and moves each diaphragm blade unit 51 individually, and the center of the exposure field 4a is matched to the test object of subject.

When Judgment unit 85 judges that part or all of exposure field 4a exceed the detection range of X-ray detector 4 by moving of the center of exposure field 4a, operating information processing unit 8 send the moving amount and the moving direction of the exposure field 4a to imaging system control unit 101. Imaging system control unit 101 controls imaging system drive unit 102, and tabletop 2, X-ray tube 3, and X-ray detector 4 do relative movement, and the center of the exposure field 4a is matched to the test object of subject.

Figure 13:
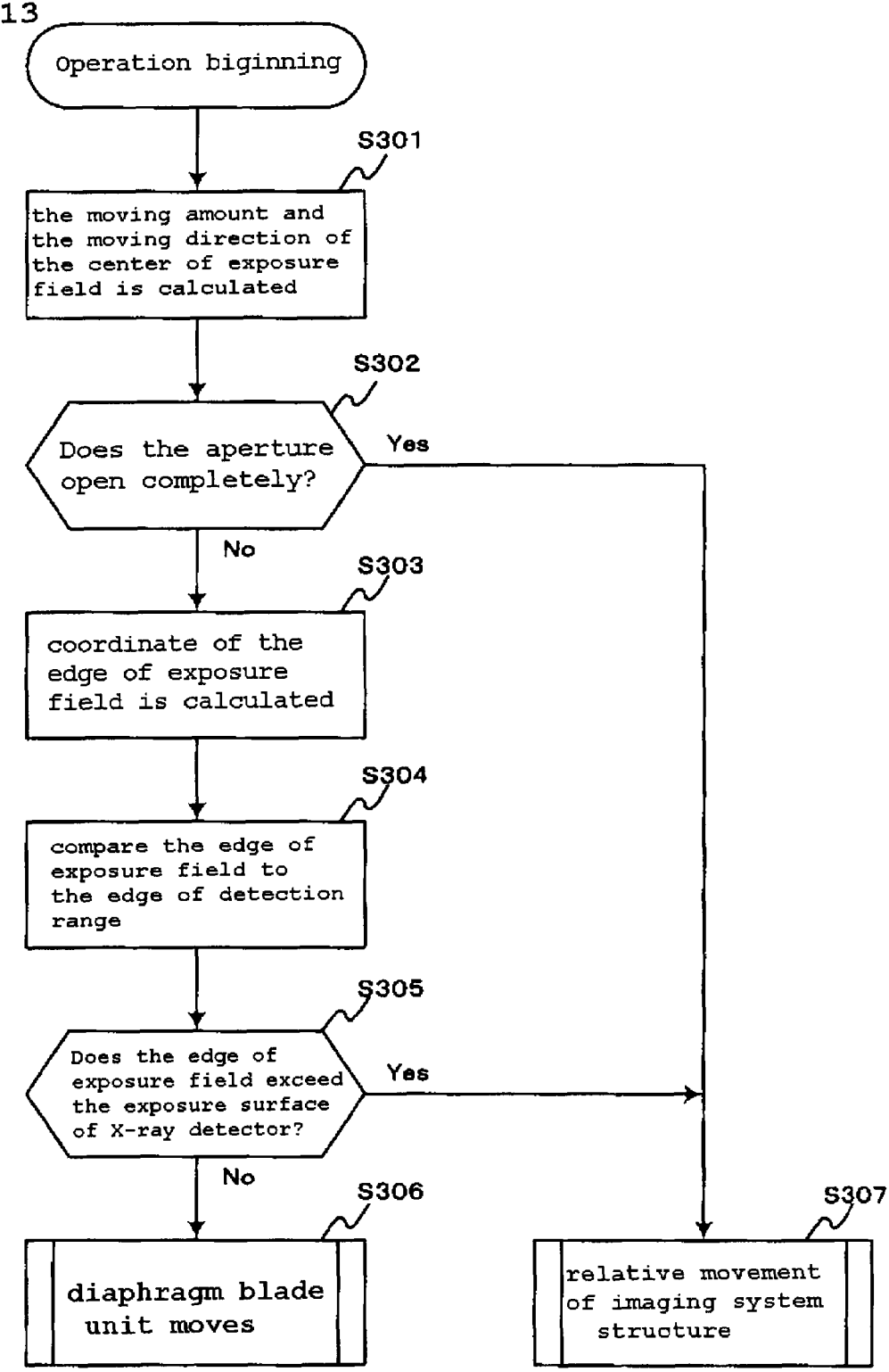
FIG. 13 is a flowchart of operating procedure by the center transfer operation unit.

Operating procedure by center transfer control unit 74 will be explained in reference to FIG. 13. FIG. 13 is a flowchart of operating procedure by the center transfer operation unit.

Operating information processing unit 8 receives instruction from center transfer operation unit 74. Moving amount compute unit 81 calculates the moving amount of the center of exposure field 4a based on the position of movement origin at center of exposure field 4a and the position information of moving destination at center of exposure field 4a (S301).

Judgment unit 85 judges whether the distance (aperture) between each diaphragm blade unit 51 opens completely based on aperture information on diaphragm blade unit 51 maintained in aperture information holding unit 84 (S302). When the distance (aperture) between each diaphragm blade unit 51 is completely open (S302; Yes), the imaging system structure does relative movement (S307).

When the distance (aperture) between each diaphragm blade unit 51 is not completely open (S306; No), operating information processing unit 8 calculates coordinates on the edge of the exposure field 4a based on information at position of moving destination at center of exposure field 4a and the aperture information on diaphragm blade unit 51 preserved in aperture information holding unit 84 (S303). Operating information processing unit 8 calculates coordinates on the edge of detection range of -ray detector 4 based on location information of imaging system position information holding unit 83 maintained in tabletop 2 and location information of X-ray detector 4.

Judgment unit 85 compares the edge of the exposure field 4a and the edge of the detection range of X-ray detector 4 (S304). When judgment unit 85 judges that at least one of the edges of exposure field 4a exceeds the detection range of -ray detector 4 (S304; Yes), and moving of the imaging system structure begins (S307). When judgment unit 85 judges that exposure field 4*a* enters the detection range (S304; No), and moving of diaphragm blade unit 51 begins (S306).

Figure 14:
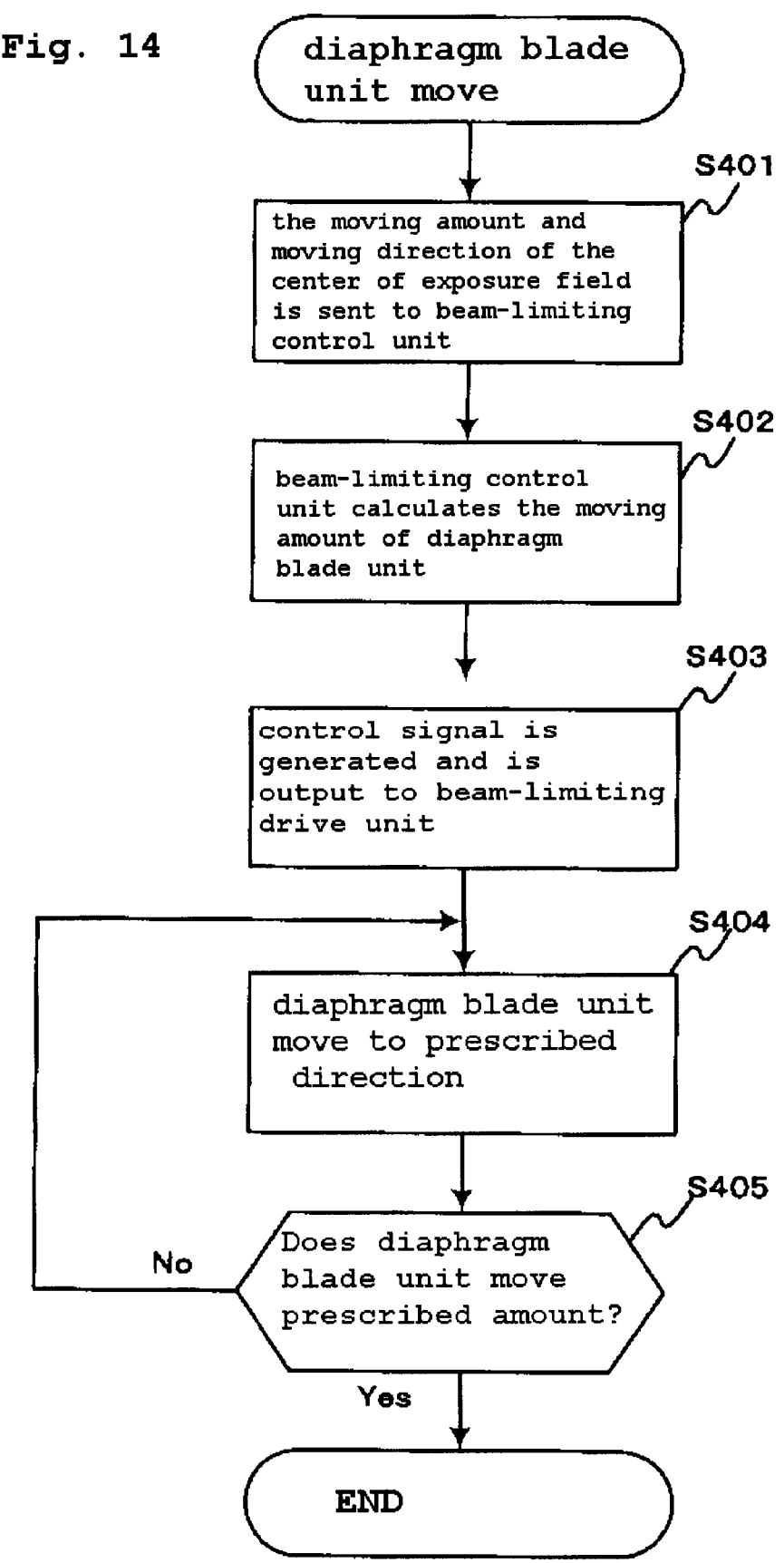
FIG. 14 is a flowchart of procedure of the diaphragm blade unit moves.

Moving of diaphragm blade unit 51 will explained in reference to FIG. 14. FIG. 14 is a flowchart of procedure of the diaphragm blade unit moves.

The moving amount and the moving direction of the center of the exposure field 4*a* is sent to beam-limiting control unit 62 in FIG. 14 (S401). Beam-limiting control unit 62 calculates the moving amount and the moving direction of diaphragm blade unit 51 based on the moving amount and the moving direction of the center of the exposure field 4*a* (S402). Beam-limiting control unit 62 generates the control signal from the moving amount and the moving direction of diaphragm blade unit 51, and output it to beam-limiting drive unit 52 (S403).

Beam-limiting drive unit 52 moves diaphragm blade unit 51 (S404). When beam-limiting drive unit 52 moves diaphragm blade unit 51 prescribed amount (S405; Yes), beam-limiting drive unit 52 stops moving of diaphragm blade unit 51.

When the operator directs the moving destination at the center of the exposure field 4*a* by center transfer control unit 74, each diaphragm blade unit 51 follows to the movement of the center of the exposure field 4*a*. And, the center of the exposure field 4*a* can be easily matched to the test object of subject after is changed.

Figure 15:
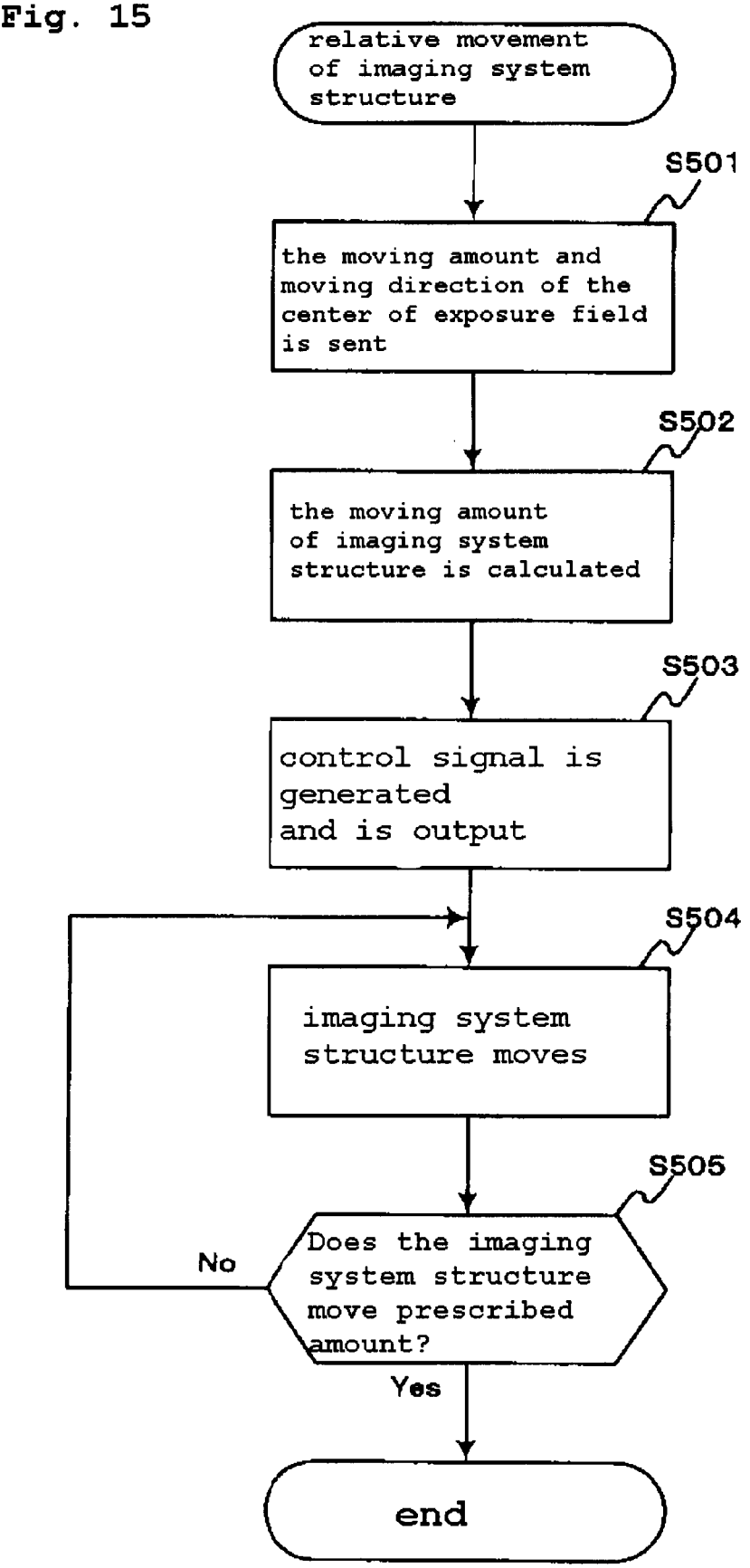
FIG. 15 is a flowchart of procedure of a imaging system construction is relative movement.

Next, the relative movement of the imaging system structure will explained in reference to FIG. 15. FIG. 15 is a flowchart of procedure of an imaging system construction is relative movement.

As shown in FIG. 15, the moving amount and the moving direction of the center of the exposure field 4*a* is sent to imaging system control unit 101 (S501). Imaging system control unit 101 calculates amount where X-ray tube 3 and X-ray detector 4 move along Z-way and amount where tabletop 2 moves in X-way from moving amount and moving direction the center of exposure field 4*a* (S502).

Imaging system control unit 101 generates the control signal from the calculated moving amount, and output it to imaging system drive unit 102 (S503). The imaging system structure moves respectively (S504).

When the imaging system structure moves prescribed amount (S105; Yes), imaging system drive unit 102 stops moving of the imaging system structure. The center of the exposure field 4*a* can be easily matched to the test object of subject after is changed.

Next, the relative movement of the imaging system structure will be explained by illustrating the movement of the center of the exposure field 4*a*.

Figure 16A:
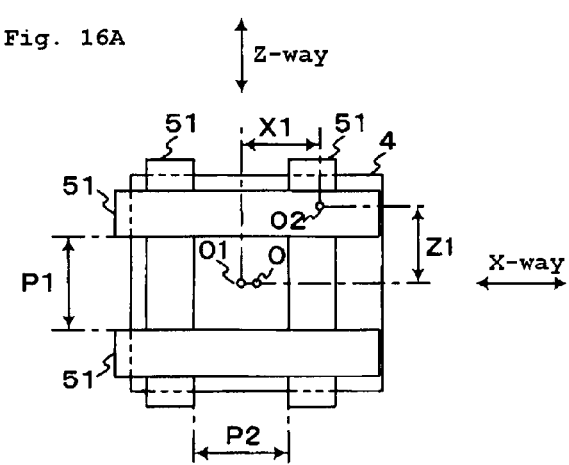
FIGS. 16A to 16C are a figure for explaining the mode that the imaging system construction is relative movement.
Figure 16B:
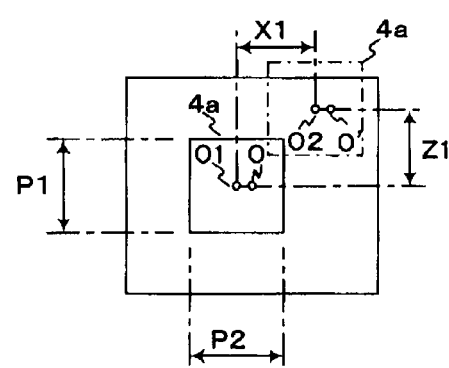
Figure 16C:
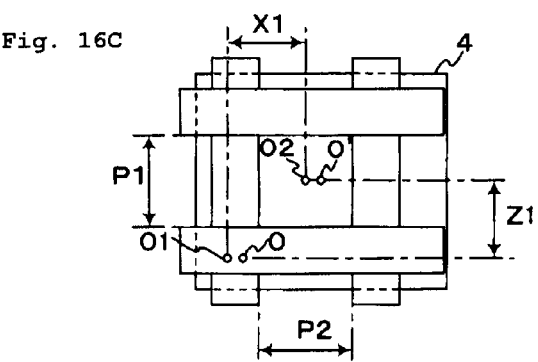

FIGS. 16A to 16C are a figure for explaining the mode that the imaging system construction is relative movement. FIG. 16A shows the position of the movement origin at the center of the range detection of X-ray detector 4 and the position O1 of the movement origin at the center of the exposure field 4*a*.

By operating center transfer operation unit 74, the center of exposure field 4*a* move to the longer direction of tabletop 2 (Z-way) to Z1, move to the shorter direction of tabletop 2 (X-way) to X1. And, the center of exposure field 4*a* becomes the position O2 from the position O1. FIG. 16B shows the exposure field 4*a* exceeds the detection range of X-ray detector 4 when the center of exposure field 4*a* is position O2. FIG. 16 shows exposure field 4*a* and doesn't shows diaphragm blade unit 51.

As shown in FIG. 16B, when judgment unit 85 judges that exposure field 4*a* goes over the detection range of X-ray detector 4, imaging system control unit 101 controls imaging system drive unit 102 and does relative movement of the imaging system structure. And, the center of exposure field 4*a* changes the position O2 from the position O1. The center of detection range of X-ray detector 4 changes the position O' from the position O. FIG. 16C shows state after center of exposure field 4*a* becomes position O2 from position O1.

In the second embodiment, when part or all in the exposure field 4*a* exceed the detection range of X-ray detector 4 by moving the exposure field 4*a*, diaphragm blade unit 51 is moved until the exposure field 4*a* exceeds the detection range of X-ray detector 4. When the exposure field 4*a* exceeds the detection range of X-ray detector 4, beam-limiting control unit 62 may controls beam-limiting drive unit 52 to do the movement of diaphragm blade unit 51 and the relative movement of imaging system structure continuously, and imaging system control unit 102 may controls imaging system drive unit 102.

When judgment unit 85 judges that part or all of exposure field 4*a* exceed the detection range of X-ray detector 4, imaging system control unit 101 controls imaging system drive unit 102, and tabletop 2, X-ray tube 3, and X-ray detector 4 are moved respectively. In doing so, the position of the center of detection range of X-ray detector matches position of moving destination at center of exposure field 4*a*.

Figure 17:
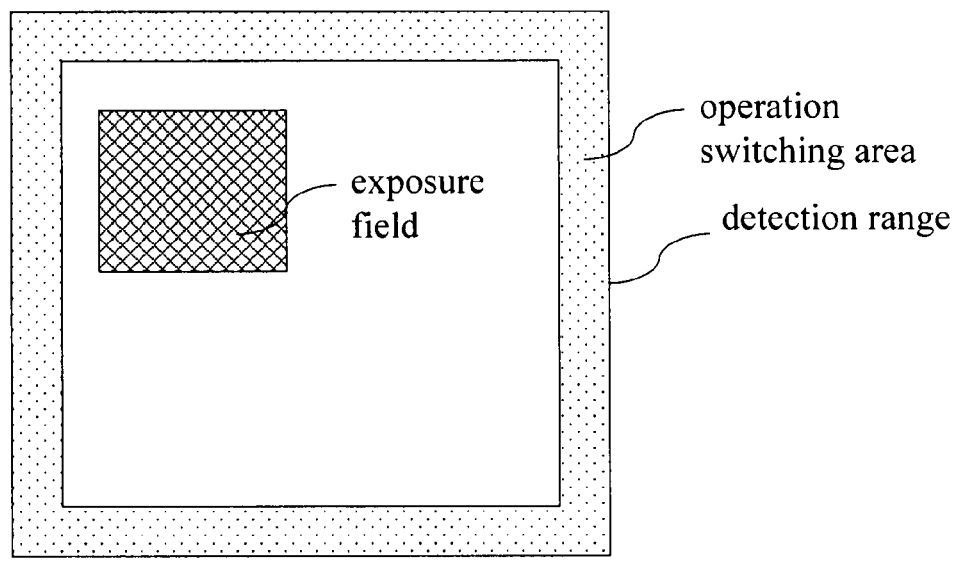
FIG. 17 is a figure of movement switch area of range of detection.
Figure 18:
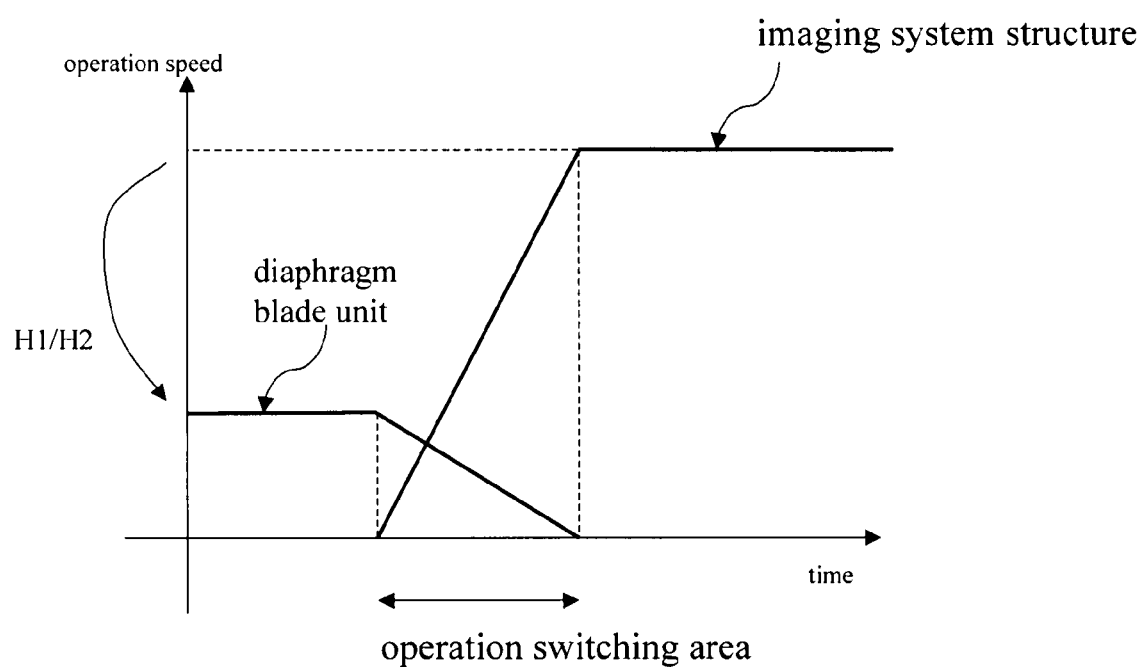
FIG. 18 is a figure of one example of change in operation speed of the movement switch area.
Figure 19:
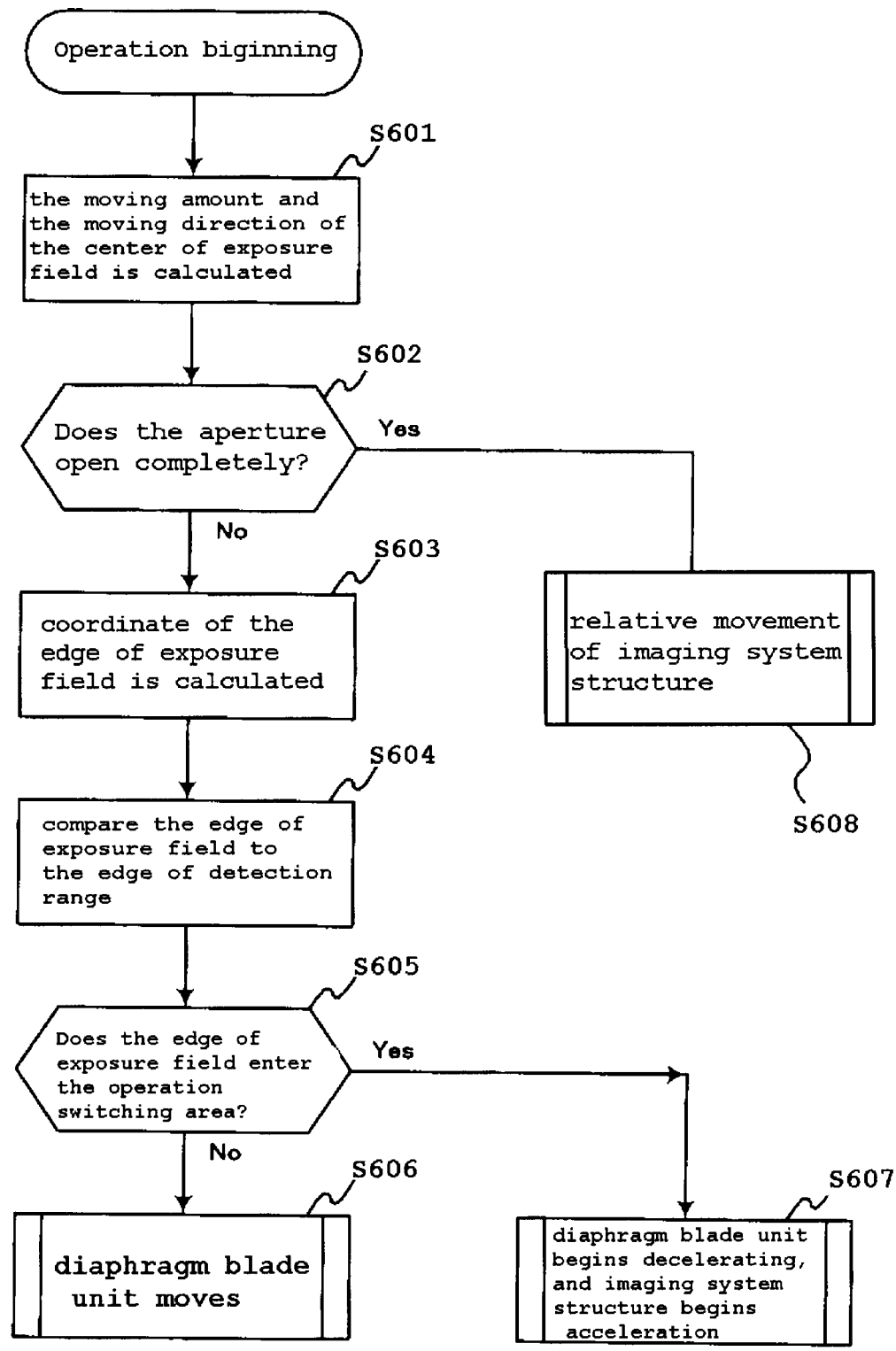
FIG. 19 is a flowchart of procedure of the movement switch area.

The operation switching area is equipped the edge of detection range. Smooth operation switch of movement of diaphragm blade unit 51 and relative movement of the imaging system structure will be explained in reference to FIGS. 17 to 19. FIG. 17 is a figure of movement switch area of range of detection. FIG. 18 is a figure of one example of change in operation speed of the movement switch area. FIG. 19 is a flowchart of procedure of the movement switch area.

Operating information processing unit 8 receives instruction from center transfer operation unit 74. Moving amount compute unit 81 calculates the moving amount of the center of exposure field 4*a* based on the position of movement origin at center of exposure field 4*a* and the position information of moving destination at center of exposure field 4*a* (S601).

Judgment unit 85 judges whether the distance (aperture) between each diaphragm blade unit 51 opens completely based on aperture information on diaphragm blade unit 51 maintained in aperture information holding unit 84 (S602). When the distance (aperture) between each diaphragm blade unit 51 is completely open (S602; Yes), the imaging system structure does relative movement (S608).

When the distance (aperture) between each diaphragm blade unit 51 is not completely open (S602; No), operating information processing unit 8 calculates coordinates on the edge of the exposure field 4*a* based on information at position of moving destination at center of exposure field 4*a* and the aperture information on diaphragm blade unit 51 preserved in aperture information holding unit 84 (S603). Operating information processing unit 8 calculates coordinates on the edge of detection range of -ray detector 4 based on location information of imaging system position information holding unit 83 maintained in tabletop 2 and location information of X-ray detector 4.

Judgment unit 85 compares the edge of the exposure field 4*a* and the edge of the detection range of X-ray detector 4 (S604). When judgment unit 85 judges that at least one of the edges of exposure field 4*a* enters the operation switching area of edge of detection range (S506; Yes), moving of each diaphragm blade unit 51 begins decelerating, and moving of the imaging system structure begins acceleration at the same time (S607). Flow shifts to the step S305 in FIG. 13.

To be concrete, as shown in FIG. 18, a speed is controlled that it is the movement speed of each diaphragm blade unit 51=H1/H2×the movement speed of the imaging system structure. In doing so, movement on the screen is kept at a constant speed. The movement of each diaphragm blade unit 51 ends by the edge of the exposure field 4a goes out of the operation switching area. The movement speed of the imaging system structure steadies, and a relative movement is done.

When judgment unit 85 judges that the exposure field 4a doesn't enter the operation switching area (S304; No), diaphragm blade unit 51 moves (S306).

Embodiment 3

In the first and second embodiments, retention feature 11 maintains X-ray tube 3 and beam-limiting device 5. It is composed to move along the longer direction of tabletop 2, and it is composed to move X-ray detector 4 with X-ray tube 3 and beam-limiting device 5 as one body.

In the third embodiment, X-ray tube 3 and X-ray detector 4 is composed the vertical plane including the body axis of subject rotatably with one arbitrary point between X-ray tube 3 and X-ray detector 4 is centers.

Figure 20:
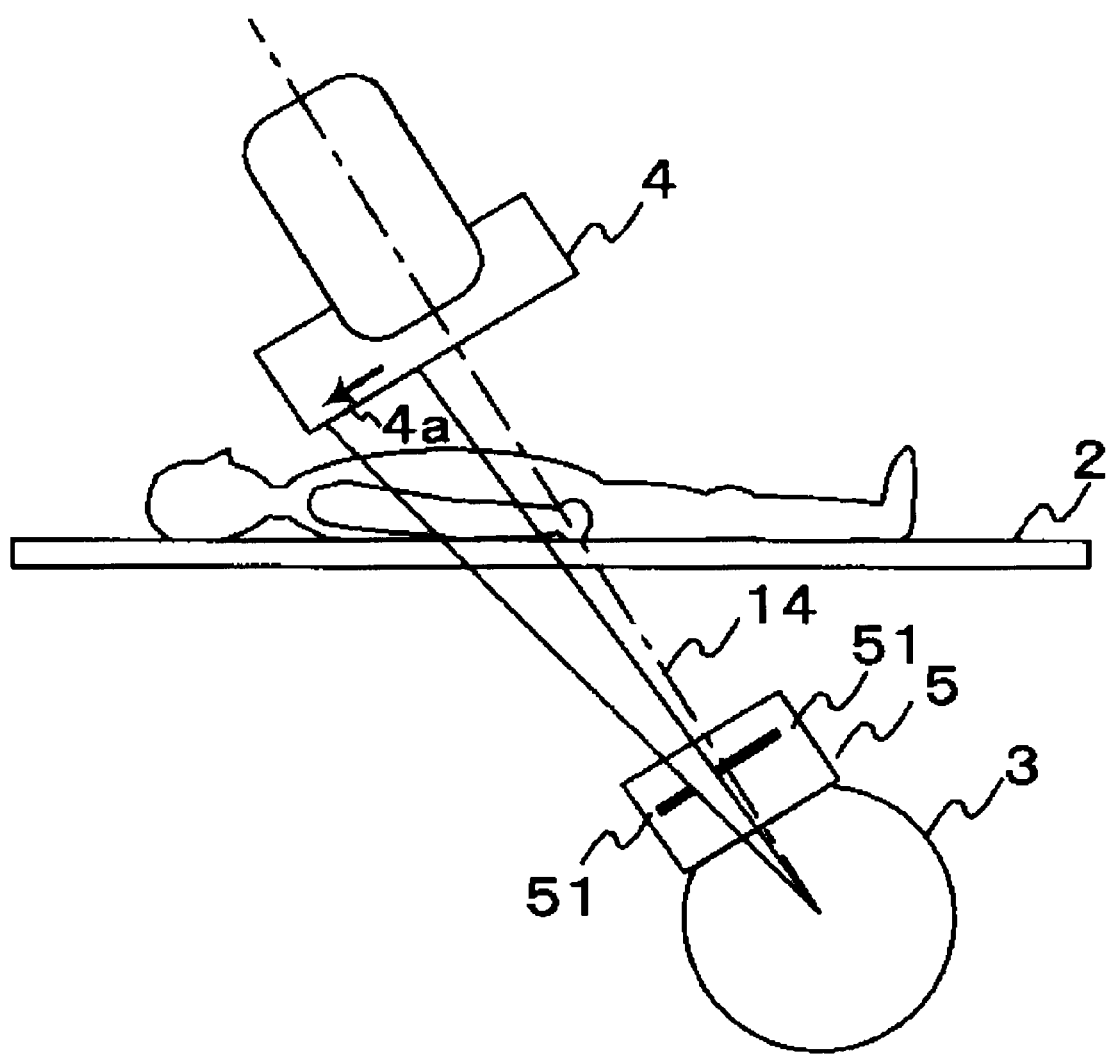
FIG. 20 is a conceptual diagram of the X-ray diagnostic apparatus according to a third embodiment.

FIG. 20 is a conceptual diagram of the X-ray diagnostic apparatus according to a third embodiment. As shown in FIG. 20, C-arm 14 (imaginary line in FIG. 20) is supported to the retention feature rotatably. X-ray tube 3 and diaphragm blade unit 51 are installed on part of C-arm 14. X-ray detector 4 is installed on other edges of C-arm 14.

As shown in FIG. 20, C-arm 14 (chain line in FIG. 20) rotates, and the exposure field 4a approaches the test object of subject. When the center of the exposure field 4a is not suitable for the test object of subject, the center of the exposure field 4a can be matched to the test object of subject by individually moving diaphragm blade unit 51.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus, comprising:
a tabletop configured to support a subject;
an X-ray tube configured to irradiate X-rays and disposed on one side of the tabletop;
an X-ray detector configured to detect X-rays that penetrate the subject and disposed on the other side of the tabletop;
four diaphragm blade units located between the X-ray tube and the tabletop, a first pair of diaphragm blade units configured to move antithetically in a longer direction of the tabletop, and a second pair of diaphragm blade units configured to move antithetically in a shorter direction of the tabletop, each of the four diaphragm blade units configured to form an exposure field on the X-ray detector;
a beam-limiting drive unit configured to drive each of the four diaphragm blade units individually;
a center transfer control unit configured to indicate a moving destination at a center of the exposure field;
a beam-limiting control unit configured to receive information about a moving amount and a moving direction when the center of the exposure field moves, to control the beam-limiting drive unit to move each of the four diaphragm blade units individually, and to form the exposure field of the moving center that is concentric therewith; and
an operating information processing unit configured to calculate the moving amount and the moving direction of the center of the exposure field when receiving an indication from the center transfer operation unit and to output the calculated moving amount and moving direction of the center of the exposure field to the beam-limiting control unit.

2. The apparatus according to claim 1, further comprising:
a display control unit configured to display the exposure field on the display and the center position of the exposure field of the X-ray detector is made to correspond to a standard position in the display.

3. The apparatus according to claim 1, further comprising:
a display control unit configured to display the exposure field on the display and the center position of the exposure field of the X-ray detector is made to correspond to a predetermined standard position in the display.

4. The apparatus according to claim 1, wherein each of the four diaphragm blade units narrows a detection range where X-rays of the X-ray detector are detected from the longer direction and the shorter direction of the tabletop, respectively, and forms the exposure field on the X-ray detector.

5. An X-ray diagnostic apparatus, comprising:
a tabletop configured to support a subject;
an X-ray tube configured to irradiate X-rays and disposed on one side of the tabletop;
an X-ray detector configured to detect X-rays that penetrate the subject and disposed on the other side of the tabletop;
four diaphragm blade units located between the X-ray tube and the tabletop, a first pair of diaphragm blade units configured to move antithetically in a longer direction of the tabletop, and a second pair of diaphragm blade units configured to move antithetically in a shorter direction of the tabletop, each of the four diaphragm blade units configured to form an exposure field on the X-ray detector;
a beam-limiting drive unit configured to drive each of the four diaphragm blade units individually;
an imaging system drive unit configured to drive the tabletop, the X-ray tube, and the X-ray detector, respectively, so that a detection range of X-ray detector is relative to movement in the longer direction and the shorter direction of the tabletop;
an aperture information holding unit configured to hold aperture information about the longer direction of the tabletop and aperture information about the shorter direction of the tabletop;
a center transfer operation unit configured to indicate the moving direction of a center of the exposure field; and
a judgment unit configured to judge whether part or all of the exposure field exceeds the detection range of the X-ray detector or part or all of the exposure field enters an operation switching area formed at an edge of the detection range based on a moving amount and a moving direction information about the center of the exposure field and the aperture information held in the aperture information holding unit.

6. The apparatus according to claim 5, further comprising:
an imaging system control unit configured to control the imaging system drive unit, to move the tabletop, the X-ray tube, and the X-ray detector, and to form an exposure field that is centered on a position of a moving destination when the judgment unit judges that part or all of the exposure field exceeds the detection range; and a beam-limiting control unit configured to control the beam-limiting drive unit to move the each of the four diaphragm blade units individually, and to form the exposure field that is centered on the position of the moving destination when the judgment unit judges that all of exposure field enters the detection range.

7. The apparatus according to claim 5, wherein the beam-limiting controls the imaging system drive unit to move the each of the four diaphragm blade units individually until the exposure field exceed the detection range of the X-ray detector, and the imaging system control unit controls the imaging system drive unit to move the tabletop, the X-ray tube, and the X-ray detector from the exposure field exceed the detection range of the X-ray detector.

8. The apparatus according to claim 5, wherein, the beam-limiting control unit controls the beam-limiting drive unit to move the each of the four diaphragm blade units individually until part or all of the exposure field enters the operation switching area and the imaging system control unit controls the imaging system drive unit to begin moving of the tabletop, the X-ray tube and the X-ray detector, and the beam-limiting control unit controls the beam-limiting drive unit to decelerate the speed at which each the of the four diaphragm blade units is individually moved from part of the exposure field that enters the operation switching area and to form the exposure field that is centered on a position of a moving destination.

9. The apparatus according to claim 5, further comprising:

a display control unit configured to display the exposure field on the display and the center position of the exposure field of the X-ray detector is made to correspond to a standard position in the display.

10. The apparatus according to claim 5, wherein the four diaphragm blade units narrow the detection range where X-rays of the X-ray detector are detected from the longer direction and the shorter direction of the tabletop, respectively, and forms the exposure field on the X-ray detector.

* * * * *